United States Patent
Lewis, Jr. et al.

(10) Patent No.: US 10,092,271 B2
(45) Date of Patent: Oct. 9, 2018

(54) ULTRASOUND TRANSDUCER PROBE AND METHODS

(75) Inventors: George K. Lewis, Jr., Ithaca, NY (US); William L. Olbricht, Ithaca, NY (US); Steven Gelber, Ithaca, NY (US); George K. Lewis, Sr., Andover, MA (US)

(73) Assignee: CORNELL UNIVERSITY, Ithaca, NY (US)

(*) Notice: Subject to any disclaimer, the term of this patent is extended or adjusted under 35 U.S.C. 154(b) by 827 days.

(21) Appl. No.: 14/110,866

(22) PCT Filed: Apr. 13, 2012

(86) PCT No.: PCT/US2012/033632
§ 371 (c)(1),
(2), (4) Date: Aug. 15, 2014

(87) PCT Pub. No.: WO2012/142493
PCT Pub. Date: Oct. 18, 2012

(65) Prior Publication Data
US 2014/0350397 A1    Nov. 27, 2014

Related U.S. Application Data

(60) Provisional application No. 61/472,087, filed on Apr. 13, 2011.

(51) Int. Cl.
*A61B 8/00* (2006.01)
*A61B 8/08* (2006.01)
*A61B 5/00* (2006.01)

(52) U.S. Cl.
CPC .......... *A61B 8/4494* (2013.01); *A61B 5/4356* (2013.01); *A61B 8/0866* (2013.01);
(Continued)

(58) Field of Classification Search
USPC .......................................................... 600/438
See application file for complete search history.

(56) References Cited

U.S. PATENT DOCUMENTS

| 4,204,435 A | * | 5/1980 | Bridoux | .................. A61B 8/08 |
| | | | | 73/626 |
| 4,569,356 A | | 2/1986 | Kyozuka et al. | |

(Continued)

FOREIGN PATENT DOCUMENTS

| GB | 1348154 | 3/1974 |
| JP | 2006247130 A | 9/2006 |
| WO | WO2004037091 A1 | 5/2004 |

OTHER PUBLICATIONS

International Application No. PCT/US2012/033632, International Preliminary Report on Patentability, dated Oct. 15, 2013.
(Continued)

*Primary Examiner* — Joel F Brutus
(74) *Attorney, Agent, or Firm* — Heslin Rothenberg Farley & Mes; George Blasiak

(57) ABSTRACT

There is set forth herein a uterine probe having one or more transducer for detecting a uterine parameter. The one or more parameter can be a fetal heart rate. The one or more parameter can be uterine contraction. In one embodiment a uterine probe can include a transducer operative to emit sound waves for detection of a fetal heart rate (FHR). In one embodiment a uterine probe can include a transducer operative to emit sound waves for detection of a uterine contraction. The one or more transducer can be of a common technology or can be of different technology. In one embodiment a uterine probe can include one or more transducer that is operative to be driven in different signaling configurations. A first signaling configuration can be a signaling configuration for detection of a fetal heart rate. A second signaling configuration can be a signaling configuration for detection of uterine contraction.

35 Claims, 24 Drawing Sheets

(52) U.S. Cl.
CPC ............ *A61B 8/4477* (2013.01); *A61B 8/488* (2013.01); *A61B 8/5223* (2013.01); *A61B 8/54* (2013.01); *A61B 8/56* (2013.01)

(56) References Cited

U.S. PATENT DOCUMENTS

| | | | |
|---|---|---|---|
| 4,582,065 A | | 4/1986 | Adams |
| 4,646,754 A | * | 3/1987 | Seale ................. A61B 3/16 600/402 |
| 4,966,152 A | | 10/1990 | Gang et al. |
| 5,119,821 A | | 6/1992 | Tuchler |
| 5,305,756 A | | 4/1994 | Entrekin et al. |
| 6,048,323 A | | 4/2000 | Hon |
| 6,102,860 A | | 8/2000 | Mooney |
| 7,637,869 B2 | | 12/2009 | Sudol |
| 7,927,280 B2 | | 4/2011 | Davidsen |
| 9,024,507 B2 | | 5/2015 | Lewis et al. |
| 2001/0032511 A1 | * | 10/2001 | Nagai ................ A61B 8/4281 73/618 |
| 2004/0242999 A1 | * | 12/2004 | Vitek ................ A61B 17/2202 600/437 |
| 2006/0074318 A1 | | 4/2006 | Ahmed et al. |
| 2007/0260154 A1 | * | 11/2007 | Rapoport ............ A61B 5/0444 600/528 |
| 2008/0189932 A1 | | 8/2008 | Sliwa et al. |
| 2010/0016744 A1 | | 1/2010 | Brost et al. |
| 2010/0262013 A1 | * | 10/2010 | Smith .................... A61B 8/00 600/459 |
| 2011/0125025 A1 | | 5/2011 | Hart et al. |
| 2011/0160591 A1 | | 5/2011 | Hart et al. |
| 2011/0285244 A1 | | 11/2011 | Lewis et al. |
| 2013/0046230 A1 | | 2/2013 | Lewis et al. |

OTHER PUBLICATIONS

International Application No. PCT/US2012/033632, Written Opinion of the International Searching Authority, dated Nov. 30, 2012.
CN101675469A, Mar. 17, 2010 (cited with English language counterpart WO2008/135922A).
Jie and Yang Renjie eds. *Medical Imaging Dictionary*. Beijing: Beijing Science & Technology Press, 1999. pp. 216-219.
Office Action from People's Republic of China; 201280029034.2; dated Jun. 8, 2016 (cited with original version in Chinese language and with English translation).
Office Action from the People's Republic of China; Application No. 201280029034.2; dated Mar. 30, 2015 (cited with original version in Chinese language and with English translation).
Office Action from the People's Republic of China; Application No. 201280029034.2; dated Nov. 23, 2015 (cited original version in Chinese language and with English translation).
J. Smith, "*Fetal Health Assessment using Prenatal Diagnostic Techniques*" Current Opinion Obstetrics Gynecology, 20:152-6, Apr. 1, 2008, accessed Jul. 17, 2018.
RK Freeman, et al. "*Fetal Heart Rate Monitoring*" 3$^{rd}$ Edition, ISBN: 0-7817-352406, Philadelphia PA, Lippincott, Williams, & Wilkins, 2003, accessed Jul. 17, 2018.
NH Lauersen, et al. "*A New Technique for Improving the Doppler Ultrasound Signal for Fetal Heart Rate Monitoring*" Amer. J. Obstetrics Gynecology 128(3):300-2, 1977, accessed Jul. 17, 2018.
LL Case, et al. "*Ultrasound Monitoring of Mother and Fetus*" Amer. J. Nurs 72(4):725-27, 1972, accessed Jul. 17, 2018.
G. Lewis, et al. U.S. Appl. No. 61/475,087, "*Wide-Beam Ultrasound Transducer Probe and Methods*" filed Apr. 13, 2011.
W. Olbricht, et al. "*Design and Evaluation of a Novel, Wide-Beam Transducer for Fetal Heart Rate Monitoring*" Department of Biomedical Engineering, Cornell University, Ithaca NY.
W. Olbricht, et al. "*Ultrasound Fetal Monitoring*," Department of Biomedical Engineering, Cornell University, Ithaca NY.
CCD View for US201214110866, http://ccd.fiveipoffices.org/CCD-2.1.8/html/viewCcd.html?num=us2014110866&type=application dated Jul. 18, 2018.
Global Dossier Report for US2014110866, http://globaldossier.uspto.gov/#/result/application/US/14110866/849337, dated Jul. 18, 2018.
WIPO Report for WO2012142493, https://patentscope.wipo.int/search/en/detail.jsf?docId=WO2012142493, dated Aug. 10, 2018.

* cited by examiner

ULTRASOUND TRANSDUCER PROBE AND METHODS

CROSS REFERENCE TO RELATED APPLICATIONS

This application is a National Stage application under 35 U.S.C. 371 of PCT Application No. PCT/US2012/033632, filed Apr. 13, 2012, entitled Ultrasound Transducer Probe and Methods, which claims priority to U.S. Patent Application No. 61/475,087 filed Apr. 13, 2011, entitled Wide Beam Ultrasound Transducer Probe and Methods, which is incorporated herein by reference in its entirety.

FIELD OF THE INVENTION

This invention relates to transducer based devices in general and particularly to an ultrasound transducer probe.

BACKGROUND OF THE INVENTION

Ultrasound imaging works by using high frequency sound waves and their echoes to obtain images inside the human body. A transducer probe is used to generate the sound pulses and transmit them into the body.

The sound waves travel into the body and are strongly reflected at interfaces between different types of tissue such as fat and muscle, or muscle and bone. At each interface a fraction of the sound wave is reflected and the rest transmitted through the interface to penetrate further into the tissue. This process occurs at each interface and by recording the reflected sound wave echoes an image can be produced. The reflections at the interfaces arise due to the impedance mismatch between different layers of the tissue. For instance, the impedance of the fat layer is different from that at the fat-muscle interface. This property is made use of to calculate the thickness of the tissue.

Fetal heart rate monitoring utilizes Doppler ultrasound to detect signs of fetal distress, especially in high risk patients and during labor. Current ultrasound transducers emit a narrow cylindrical ultrasound beam to detect and record the heartbeat and so have a limited and constricted fetal heart detection range. Their effectiveness is inhibited by limited detection range, patient movement, and bulkiness, so one pertinent clinical issue is the frequent readjustment of the traditional ultrasound transducer by nurses during labor. Due to shifting of the fetus or mother during birthing, the current devices can often lose the heartbeat.

During labor and delivery, the fetal heart rate is monitored by ultrasound and the strength, duration and length of uterine contractions is monitored electronically with a device called a tocometer. For a normal delivery, ultrasound can be used to monitor the baby's heartbeat externally. A normal heart rate indicates that the fetus is receiving sufficient oxygen throughout the contractions. While the fetal heart rate changes in response to labor contractions, erratic changes to fetal heartbeat during the birthing process, can indicate labor complications that may require emergency care. Since current ultrasound transducers produce parallel beams of ultrasound, approximately six cm in diameter, the personnel monitoring the delivery has to continuously change position of the current ultrasound transducers as the baby moves.

SUMMARY OF THE INVENTION

There is set forth herein a uterine probe having one or more transducer for detecting a uterine parameter. The one or more parameter can be a fetal heart rate. The one or more parameter can be uterine contraction. In one embodiment a uterine probe can include a transducer operative to emit sound waves for detection of a fetal heart rate (FHR). In one embodiment a uterine probe can include a transducer operative to emit sound waves for detection of a uterine contraction. The one or more transducer can be of a common technology or can be of different technology. In one embodiment a uterine probe can include one or more transducer that is operative to be driven in different signaling configurations. A first signaling configuration can be a signaling configuration for detection of a fetal heart rate. A second signaling configuration can be a signaling configuration for detection of uterine contraction.

DETAILED DESCRIPTION OF THE INVENTION

Figure 1:
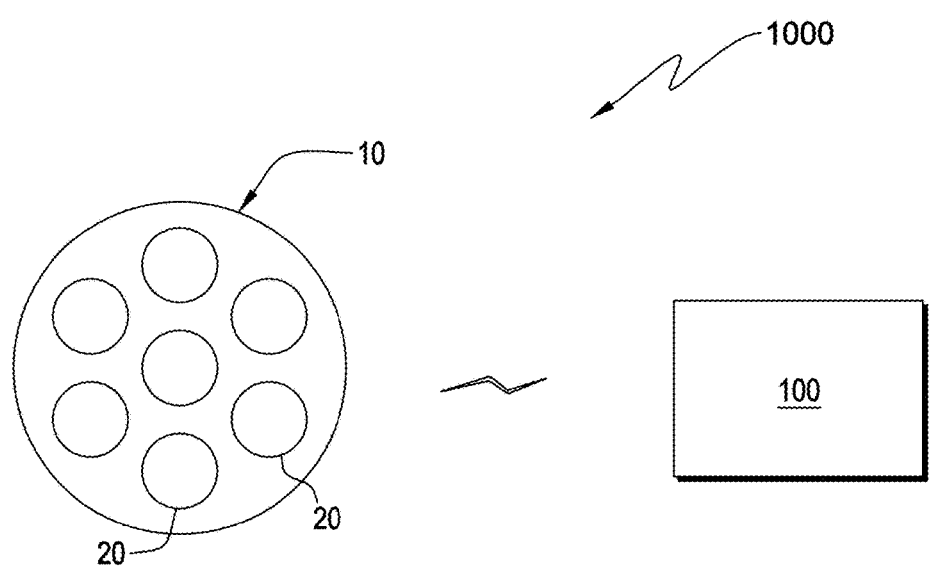
FIG. 1 is a system overview of a uterine probe system having a uterine probe.

There is set forth as shown in FIG. 1 a system 1000 having a uterine probe 10 including one or more transducer 20 for detecting a uterine parameter. The one or more parameter can be a fetal heart rate. The one or more parameter can be uterine contraction. In one embodiment a uterine probe 10 can include a transducer operative to emit sound waves for detection of a fetal heart rate (FHR). In one embodiment a uterine probe 10 can include a transducer 20 operative to emit sound waves for detection of a uterine contraction (UC). Where the one or more transducer 20 are provided by two or more transducers the two or more transducers can be of a common technology or can be of different technologies. One or more, and in one embodiment, each transducer 20 of probe 10 can be provided by a piezoelectric element, e.g., a lead zirconate titanate (PZT) transducer.

Figure 24:
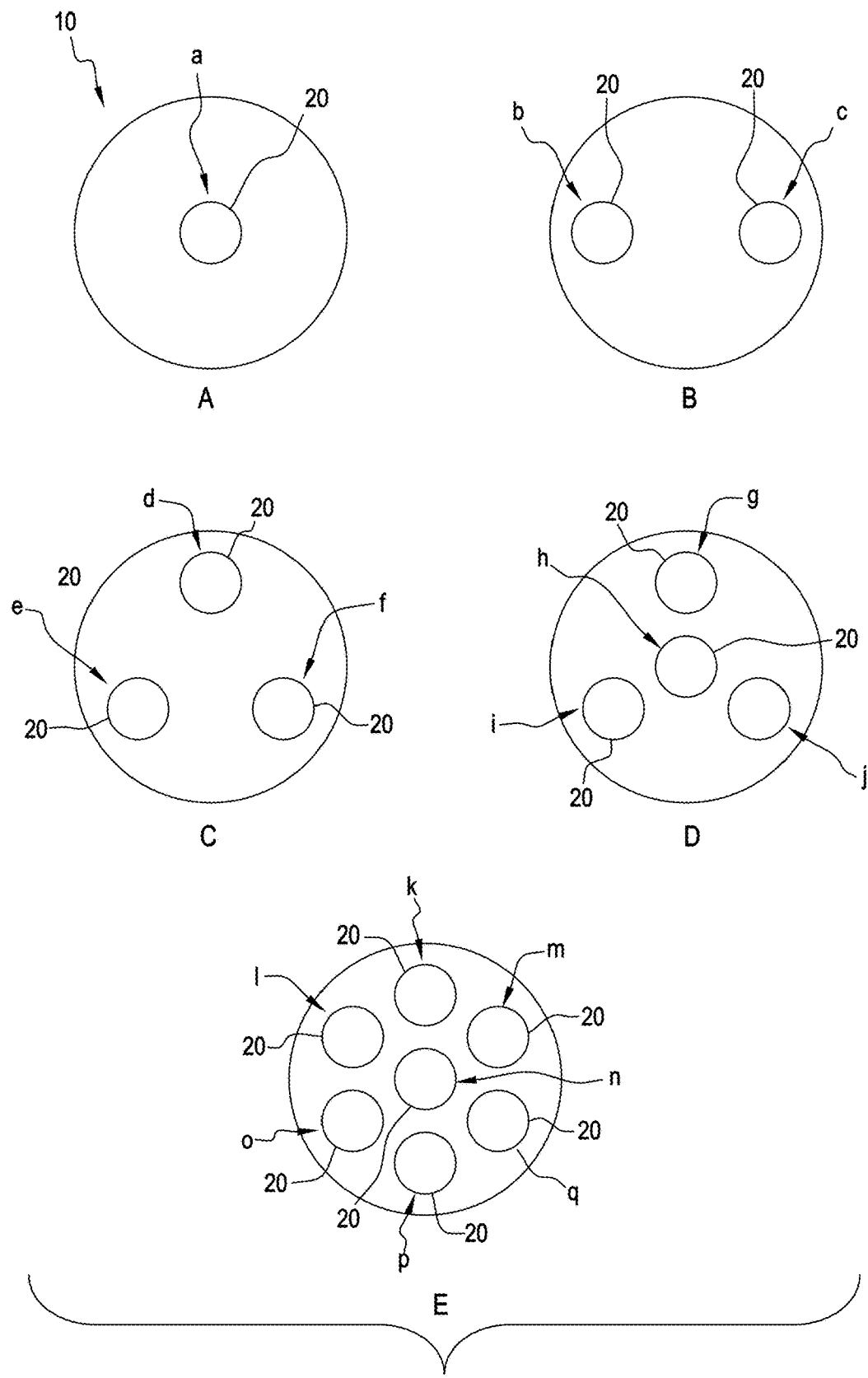
FIG. 24 is an overview diagram illustrating various alternative configurations for a probe.

In one embodiment a uterine probe 10 can include one or more transducer 20 that is operative to be driven in different signaling configurations. A first signaling configuration can be a signaling configuration for detection of a fetal heart rate. A second signaling configuration can be a signaling configuration for detection of uterine contraction. In one embodiment, a certain transducer 20, e.g., any one of transducer 20 as shown in FIG. 24 can be operated in accordance with each of the first signaling configuration, e.g., at a first time period, and the second signaling configuration, e.g., at a second time period. System 1000 can include a processing unit 100 for processing signals output by probe 10. Processing unit 100 is depicted as being external to probe 10, but can also be co-located at probe 10, e.g., disposed in a housing of probe 10. A transducer 20 of probe 10 can operate in accordance with one or more signaling configuration and one or more modes. A probe 10 can feature one or more operating profile defined by a coordination of operation between various transducers of the probe 10.

A transducer 20 of probe 10 can include various acoustical features. In one embodiment a first transducer of a probe includes a first associated acoustical lens for diverging an acoustical field and a second transducer of a probe can include a second associated acoustical lens for diverging an acoustical field. In another aspect a probe 10 can be configured to position the first transducer and the second transducer so that their respective imaging axes are non-parallel to one another.

In a cycling mode, a transducer 20 can cycle between an FHR signaling configuration and a UC signaling configuration. A cycling mode can be adaptive or non adaptive. With an adaptive cycling mode active a cycling mode can be exited on the sensing of a sensed condition or on de-energization of probe 10. The sensed condition can be signal level of a transducer of probe 10. Probe 10 can be configured so that with a non-adaptive cycling mode active, probe 10 is restricted from exiting from a cycling mode except for responsively to a de-energization of probe 10. In a constant mode, transducer 20 can constantly drive transducer 20 in accordance with a certain signaling configuration, e.g., an FHR signaling configuration and a UC signaling configuration. A constant mode can be adaptive or non adaptive. With an adaptive constant mode active a constant mode can be exited (de-activated) on the sensing of a sensed condition or on de-energization of probe 10. The sensed condition can be a signal level of a transducer of probe 10. Probe 10 can be configured so that with a non-adaptive constant mode active probe 10 is restricted from exiting a current switching configuration except for responsively to a de-energization of probe 10.

Regarding signaling configurations of a transducer 20, signaling configurations of transducer 20 can be intermittent or continuous. When a signaling configuration of transducer 20 is intermittent, a certain transducer 20 can be controlled to transition intermittently between emission periods and detection periods. When a signaling configuration of transducer 20 is continuous, transducer 20 can continuously emit a waveform without intermittently executing detection periods, or alternatively can continuously detect for reflected waveforms without intermittently executing emission periods.

Various examples of uterine probes and systems having uterine probes are set forth herein including with reference to U.S. Provisional Application 61/475,087 presented herein with reformatting including reformatting to avoid reference numeral duplication.

[Beginning of U.S. Patent Application No. 61/475,087]

There is set forth herein an ultrasound transducer probe for use in monitoring a target. The ultrasound transducer probe can include diverging ultrasound beams increasing a monitoring volume of a target.

Figure 2:
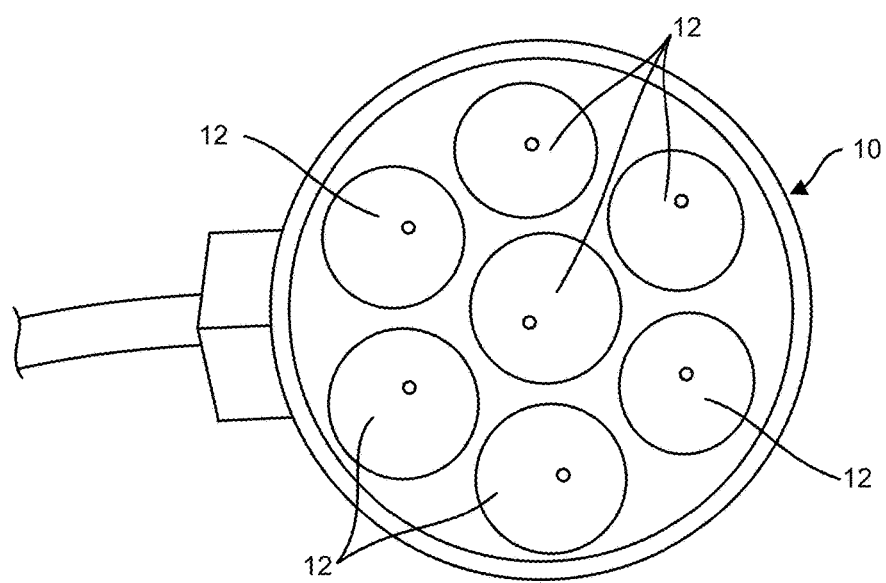
FIG. 2 is a representation of a wide-beam fetal monitoring transducer probe with seven independent wide-beam ultrasound transducer elements.

One representation of a wide-beam ultrasound transducer probe 10 is shown in FIG. 2. The transducer probe can be fabricated from ultrasound transducer elements 12 provided in one embodiment by piezoelectric, e.g., lead zirconate titanate (PZT) elements 12. Ultrasound transducer elements 12 in one embodiment can be 10 mm in diameter.

Figure 5:
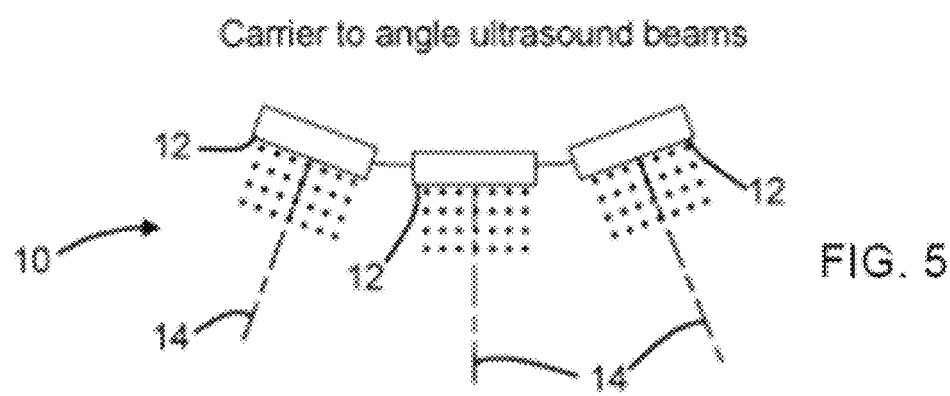
FIG. 5 is a representation of a plurality of ultrasound transducer elements arranged to have imaging axes extending in non-parallel directions.

In one embodiment of probe 10 the ultrasound transducer elements 12 can be secured in a lens carrier (FIG. 2 and FIG. 3) in a 10-30 degree diverging setting that directs an imaging axis 14 of each ultrasound transducer element 12 in a certain direction so that in one embodiment each imaging axis 14 extends in a direction nonparallel with each other imaging axis 14 (FIG. 5). Such configuration generates a field of plane-wave ultrasound beams.

Figure 6:
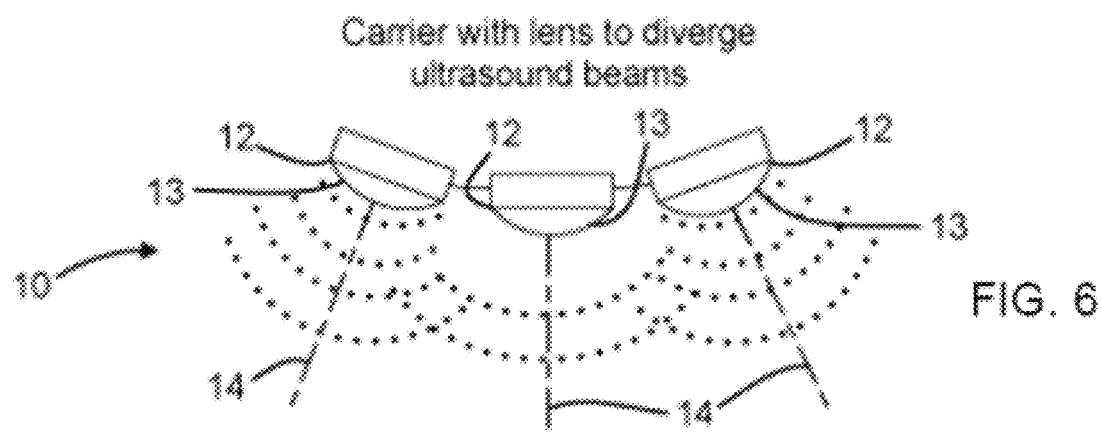
FIG. 6 is a representation of a plurality of ultrasound transducer elements arranged to have imaging axes extending in non-parallel directions, and further including lenses for converting plane wave beams into diverging conical beams.

In one aspect, the ultrasound transducer elements 12 can be fitted with custom diverging lenses 13 (FIG. 6) which convert the plane-wave beams into diverging conical beams to additionally spread the ultrasound field, while also "filling in the holes" of the field because of the carrier and positioning of the elements (FIG. 6). In one embodiment, ultrasound transducer elements 12 can employ Doppler ultrasound, particularly useful for fetal heart rate monitoring (FHM).

Electrically, each ultrasound transducer element 12 can be wired independently to enable parallel signal processing for improved sensitivity. The ultrasound transducer elements 12 can also be connected together in parallel and be used with commercially available fetal monitoring systems e.g., the Corrometrics System available from General Electric Company.

While one representation for transducer probe 10 having various parameters is described, various parameters e.g., the number of wide beam elements, the diameter of each individual ultrasound transducer element and the degree of diverging setting for both the lens carrier and lenses may be different. Parameters that can be varied can include, but are not limited to, a number of ultrasound transducer elements (e.g., there can be one to fifteen or more wide beam ultrasound transducer elements) transducer element diameter (e.g., from 1 mm or less to 100 mm) and degree divergence (e.g., from 1 degree or less to 60 degrees or more).

Figure 3:
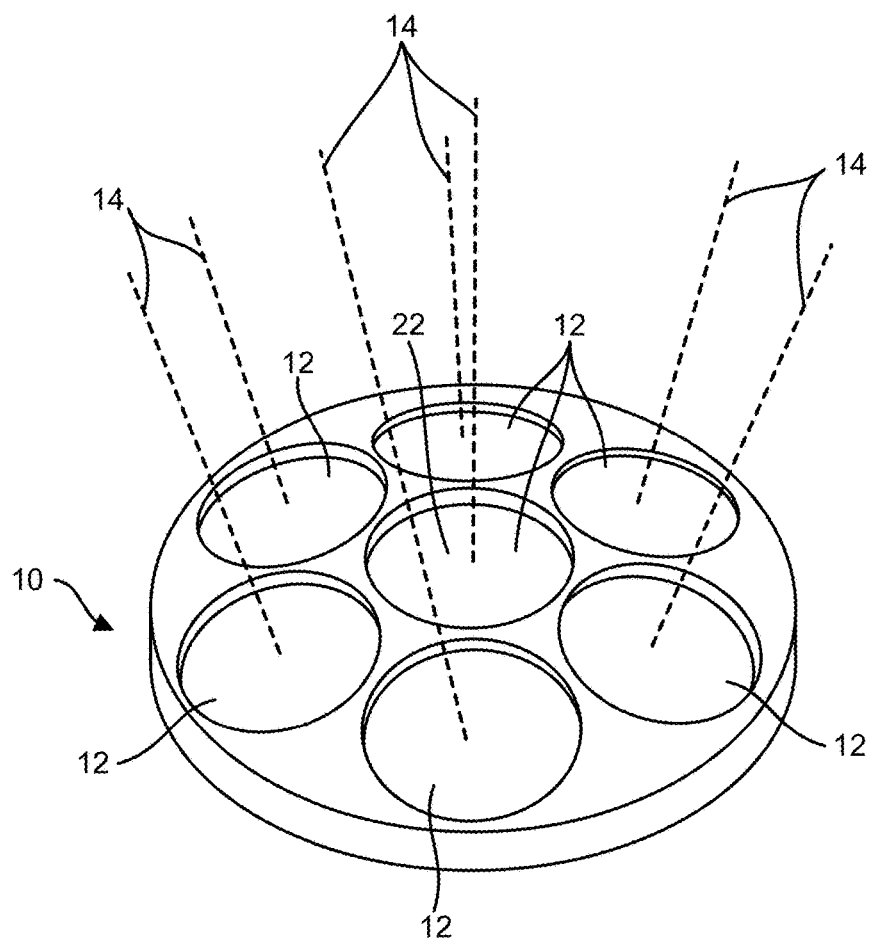
FIG. 3 is a representation of one of seven wide-beam transducer elements. One or more of the ultrasound transducer elements can be replaced with a force transducer element for use as a uterine contraction detection element. An ultrasound transducer element herein can be provided by a piezoelectric element, e.g., a lead zirconate titanate (PZT) transducer element.

One or more force transducer element useful as a uterine contraction element can be incorporated in probe 10 along with one or more wide beam ultrasound transducer element (see, e.g., FIG. 3; also, one representation shown in Appendix B) or the uterine contraction element may replace any of the wide beam ultrasound transducer elements 12 in the device (FIG. 3). In FIG. 3, the center ultrasound transducer probe element 12 is co-labeled as a force transducer element 22 to indicate that any of the ultrasound transducer elements 12 of probe 10 can be replaced by a force transducer element 22, or alternatively that a force transducer element 22 can be co-located with any ultrasound transducer element 12.

As indicated in FIGS. 2 and 3, each of the depicted ultrasound transducer elements 12 and/or force transducer elements 22 can be supported and housed in a common housing. The incorporation of different technology transducer elements in a common device, one type of transducer element particularly useful as fetal heart rate detection and the other technology transducer element particularly useful as uterine contraction elements into one device eliminates the requirement for the use of two separate devices.

In one embodiment, the fetal heart rate detection elements 12 can also be independently housed from each other, one representation shown in Appendix B.

There is set forth herein a transducer probe. The transducer probe can be utilized, e.g., for monitoring of the fetal heart rate and uterine contraction during labor. A transducer probe herein can have diverging ultrasound beams, increasing the monitoring volume of a target, e.g., a birth canal as well as monitoring uterine thickening.

A transducer probe as set forth herein provides a number of advantages.

A wide beam ultrasound transducer element probe, characterized by one or more of (a) plural ultrasound transducer elements having non-parallel imaging axes 14, and (b) one or more ultrasound transducer element having a diverging lens, is particularly useful for fetal heart rate detection. For fetal heart rate detection:

a. The "wide-beam" transducer element probe is able to better detect the baby's heart in utero over traditional narrow beam systems currently in use,
b. The wide-beam transducer element probe is less sensitive to the mother's movement or movement therapy allowing better continuous detection/monitoring,
c. The wide-beam transducer element probe reduces the acoustic intensity the fetus is subject to, and
d. The wide-beam transducer element probe works with existing commercially available ultrasound systems.

A 1-D transducer element is highly useful for uterine contraction detection. The 1-D transducer element can be a force transducer element. For uterine contraction detection, the 1-D transducer:

e. Improves measurement sensitivity,
f. Reduces the size of the traditional force transducer,
g. Enables the monitoring of contraction strength, duration and time, and
h. Measures the structure of the uterine wall throughout labor/pregnancy.

Reference is made to the accompanying drawings that form a part hereof, and in which is shown by way of illustration specific embodiments which may be practiced. These embodiments are described in detail to enable those skilled in the art to practice the invention, and it is to be understood that other embodiments may be utilized and that structural, logical and electrical changes may be made without departing from the scope of the present invention.

Regarding FIG. 2, FIG. 2 shows a wide-beam fetal monitoring transducer with seven independent wide-beam elements. Regarding FIG. 3, FIG. 3 shows a perspective view of FIG. 2. The black arrow points to one of seven wide-beam piezoelectric elements that can be replaced with a uterine contraction detection element.

Figure 4:
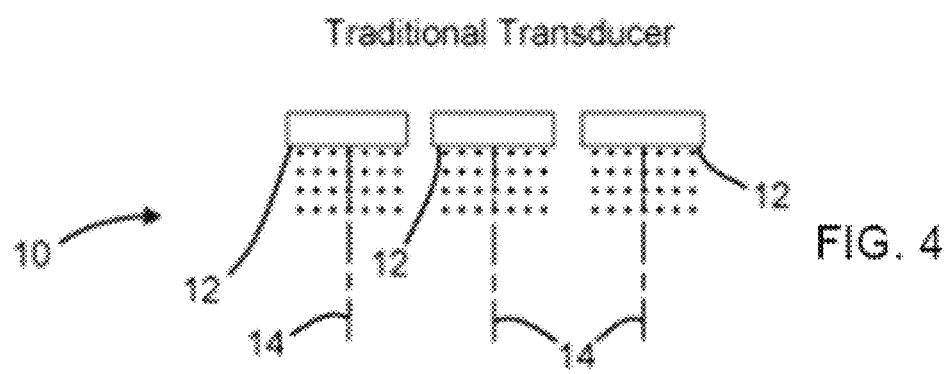
FIG. 4 is a representation of traditional transducer element in a linear array.

Regarding FIG. 4, FIG. 4 shows a representation of traditional transducers in a linear array. Regarding FIG. 5, FIG. 5 shows a representation of three elements of the transducer of a probe secured in a lens carrier with a diverging setting. Regarding FIG. 6, FIG. 6 shows a representation of the center image fitted with an added embodiment of a divergent lens to each element (three elements shown).

In the embodiments of FIGS. 5 and 6, the depicted transducer elements can be supported and housed in a common housing.

There is set forth herein, in one embodiment, an ultrasound based probe to improve fetal heart rate and uterine contraction monitoring/measurements using safe levels of ultrasound. The ultrasound based probe in one embodiment utilizes a multiple ultrasound transducer element wide-beam array to detect the fetal heart rate with Doppler ultrasound, while using a single element 1-D transducer to measure uterine contraction. The probe in one embodiment can function with available fetal heart rate monitoring systems and can reduce fetal heart rate monitoring interruption due to maternal/fetal movement during labor for more consistent fetal heart rate detection.

Details of transducer based devices, according to one embodiment, are set forth in the manuscript, entitled "Design and Evaluation of a Novel, Wide-beam Transducer for Fetal Heart Rate Monitoring" which is attached as Appendix A of previously referenced U.S. Application No. 61/475,087 and in the manuscript entitled "Ultrasound Fetal Monitoring" which is attached as Appendix B of previously referenced U.S. Application No. 61/475,087 and forms part of the present provisional patent application. The disclosure of the referenced Appendices is presented herein with reformatting to avoid reference number duplication.

[Beginning of Appendix A of U.S. Patent Application No. 61/475,087]

Regarding an objective, fetal heart rate (FHR) monitoring utilizes Doppler ultrasound to detect signs of fetal distress, especially in high risk patients and during labor. Traditionally, transducers emitting a narrow cylindrical ultrasound beam are used to record the FHR, but their effectiveness is inhibited by limited detection range, patient movement, and bulkiness. We developed a wide-beam ultrasound transducer that improved FHR detection range while functioning with available FHR monitoring systems. Regarding methods, comparisons of the wide beam transducer with a Corometrics 5700 transducer were made using a GE-Corometrics 120 Series Twin FHR Monitor on 26 subjects. Briefly, mediolateral and anteroposterior distances were measured from a defined origin on the subjects' abdomen with the wide-beam and Corometrics 5700 transducers until the FHR was no longer detected by the monitoring system. For each subject, the elliptical detection areas of both transducers were calculated and compared. Regarding results, the wide-beam transducer functioned with existing FHR monitoring systems without modification and increased the FHR detection area in 25 of 26 subjects. Paired t-test analysis found significant differences between FHR detection areas (P<0.001) for the entire subject sample. Regarding conclusions, the wide-beam reduces FHR monitoring interruption due to maternal/fetal movement during labor for more consistent FHR detection, which is important for high risk patients who require frequent monitoring.

Measurement and analysis of the fetal heart rate (FHR) has long been the standard in assessing fetal health and adequacy of blood oxygenation during the antepartum and intrapartum periods. (Smith J. Fetal health assessment using prenatal diagnostic techniques. *Curr Opin Obstet Gynecol* 2008; 20:152-6. Freeman R K, Garite T J, Nageotte M P. *Fetal Heart Rate Monitoring*. 3rd ed. Philadelphia, Pa.: Lippincott Williams & Wilkins, 2003.) One of the first direct methods of fetal assessment and diagnosis was auscultatory observation of fetal heart sounds and variations. (Smith J. Fetal health assessment using prenatal diagnostic techniques. *Curr Opin Obstet Gynecol* 2008; 20:152-6.) The complexity and scope of FHR monitoring technology has since increased, as it became possible to associate heart rate patterns, such as decelerations, accelerations, or increases in variability, with fetal diseases and conditions; thus allowing the technology to be used as a diagnostic tool. (Lauersen N H, Hochberg H M, George M E, Tegge C S, Meighan J J. A new technique for improving the Doppler ultrasound signal for fetal heart rate monitoring. *Am J Obstet Gynecol* 1977, 128(3):300-2. Case L L. Ultrasound monitoring of mother and fetus. Amer J Nurs 1972, 72(4):725-27.) Currently, Doppler ultrasound FHR monitoring remains the standard in fetal health assessment in both normal and high-risk pregnancies and deliveries. Continuous wave Doppler, as its name implies, emits continuous ultrasound waves at a known frequency (usually 1-3 MHz). As the wave moves through tissue, it can be reflected back to a receiver on the transducer. Movement in the tissue will alter the frequency of the reflected wave (Doppler shift) and this change will be detected by the transducer and monitoring unit. In contrast to continuous wave, pulse wave Doppler emits waves at specific bursts, and the time between bursts is used to receive any reflected waves. The timing of the bursts allows for a process called range gating. Essentially, the bursts and receiving periods can be timed such that only motion in a predetermined sample volume will be detected, allowing interfering information to be ignored. Additionally, pulse wave ultrasound reduces the overall exposure of the patient to ultrasound waves. Existing fetal monitoring systems are coupled with pulse wave ultrasonic transducers, which produce a straight 5-7 cm diameter ultrasound beam and are positioned on the maternal abdomen directly over the fetuses' heart for detection of the heartbeat. (Gang, A., et. al. Transducer. U.S. Pat. No. 4,966,152. Oct. 30, 1990.) Prior ultrasound transducers were further limited, having detection ranges as small as 3 cm diameter, necessitating placement exactly over the fetal heart for detection. (Gang, A., et. al. Transducer. U.S. Pat. No. 4,966,152. Oct. 30, 1990.) Such a small detection area was needed to obtain meaningful heart rate data and avoid noise interference. The development of filtering technology through autocorrelation algorithms allowed the expansion of the ultrasound beam. (Kyozuka, et al. Method and apparatus for detecting fetal heart rate by autocorrelation. U.S. Pat. No. 4,569,356. Feb. 11, 1986.) Current technology allows some flexibility in transducer placement, however, one of the major inadequacies with current FHR monitoring technology is the sensitivity to fetal and maternal movement and resulting loss of the heart rate signal, especially during labor as the fetus moves through the birth canal. This signal loss can be attributed to the still limited detection range of the ultrasound beam and its inability to measure the Doppler signal of the fetal heart. As a result, current labor protocols require the transducer to be strapped to the mothers' abdomen while she remains in a stationary, supine position and, the transducer must be repositioned by the medical staff when the signal is inevitably lost. Wireless telemetry systems have been developed to increase patient motility while still maintaining continuous fetal heart rate recording. For example, the GE Corometrics 340M uses a wireless battery powered portable transmitter that can be worn by the patient, send continuous data to a receiver from up to 1,640 ft (line of site distance) away, and is compatible with the Corometrics 170, 250, and 250cx series monitors (GE healthcare). However, sensitivity of existing transducers to fetal and maternal movement limits the application of this technology. Improvements in the transducer detection range, which would reduce sensitivity to movement, would make this technology more advantageous.

In response to limitations with the existing technology, a custom low profile, wide-beam ultrasound transducer was developed to improve upon limitations in fetal tracking and spatial heart rate detection. This technology aims to decrease the invasiveness of ultrasound FHR monitoring during labor and delivery, and to increase the mobility and comfort of the patients. A study evaluated the effectiveness of this new transducer against current technology.

Regarding materials and methods, this is set forth herein (A) technical comparison and (B) statistical analysis.

Figure 7:
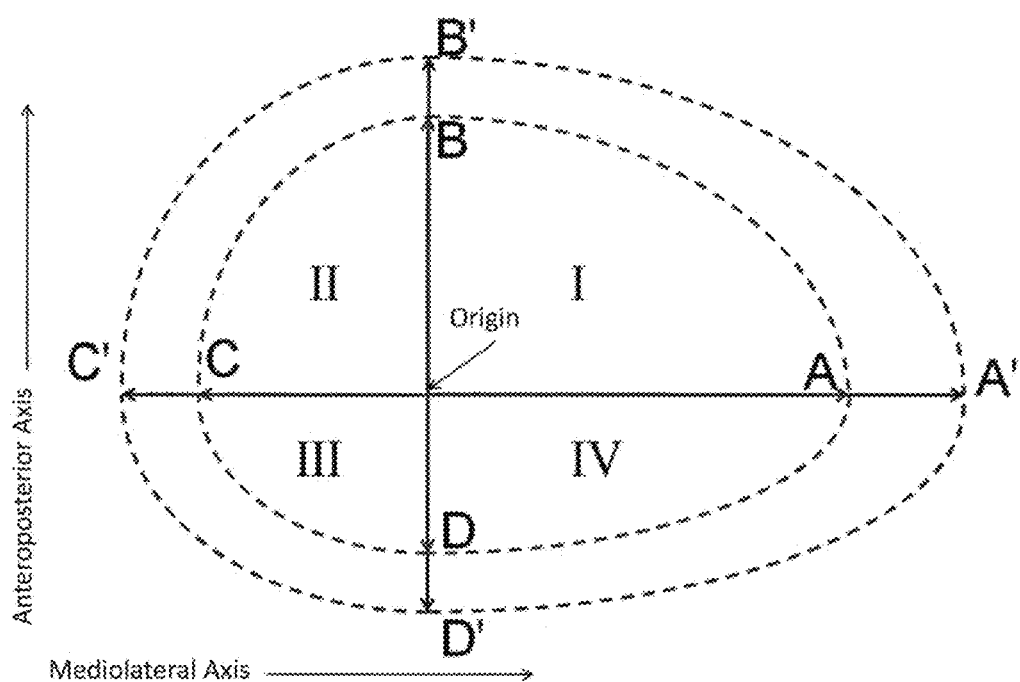
FIG. 7 is a depiction of a uterine detection area in one embodiment.

(A) Technology comparison, this wide-beam ultrasound transducer technology, designed and built at Cornell University, was compared to an existing Corometrics 5700 Ultrasonic Transducer (General Electric, Fairfield, Conn.) using a GE Corometrics 120 Series Twin Monitor (General Electric, Fairfield, Conn.). Subjects were asked to lie supine on an examination table in a comfortable position for the length of the experiment. The origin, defined as the point on the subjects' abdomen where the fetal heart beat signal was strongest by audible detection, was found with the Corometrics transducer and marked. The detection limit of the Corometrics transducer was determined by moving the transducer in four directions away from the origin along the mediolateral and anteroposterior axes (FIG. 7). The distance from the origin to the point where the heart beat was no longer detected (both audibly and by the monitor tracking) was measured and recorded for each direction. This process was repeated with our wide-beam transducer technology with the origin assumed to be at the same location in both cases. Subjects were instructed to report fetal movement during the experiments and any movement reported by the subject or observed directly was recorded.

Elliptical detection areas were calculated for each transducer using the measurements taken. Each detection area was comprised of four quarter ellipsis (I, II, III, and IV) defined by the distances from the origin (A, B, C, D) (FIG. 7). These measurement lengths were considered to be half the lengths of the major and minor axes of theoretical ellipses. The areas of the quarter ellipsis were calculated by taking one fourth of the value determined by the standard area equation of an ellipse, and the total effective coverage area was the sum of areas I, II, III, and IV. For example, to calculate the area of quarter ellipse I, the following equation would be used:

$$\text{Area} = \frac{1}{4} * \pi * A * B$$

The same process was performed with novel transducer measurements (A', B', C', D') to determine new effective detection areas.

(B) Statistical analyses. All data was collected and analyzed using Excel software (Microsoft Corporation, Redmond, Wash.). The effective coverage areas were computed and compared for each individual subject using a paired student's t-test, with $P<0.001$ being considered significant. Subjects were also grouped based on BMI ratings (Table 1). Due to small sample sizes for the underweight and obese BMI categories, analysis of these subgroups for significance was not performed.

Regarding results, the effective detection area was greater with the wide-beam transducer for 25 of 26 subjects. Detection areas and corresponding percent increases for each subject are shown in Table 2. The average detection areas for the entire subject sample as well as each of the BMI subgroups are compared in FIGS. 8 and 9. Significant ($P<0.001$) increases in the detection areas were found for the entire subject sample, as well as the normal and overweight subgroups. The average difference in detection area between the wide-beam and Corometrics transducers was 173.1, 112.5, and 259.9 $cm^2$ for the normal, overweight, and obese subgroups, respectively.

Regarding a discussion, the wide-beam transducer performed significantly better in vivo, indicating this technology shows great promise for improving fetal heart rate monitoring. The greater detection range of the wide-beam transducer shows that use of the new device during labor will require less repositioning than existing transducers. Eventual combination of this technology with existing wireless telemetry systems will greatly reduce the invasiveness of fetal monitoring during labor. A wireless system used with a transducer needing minimal or no repositioning will allow the mother to remain mobile through most of labor while maintaining continuous fetal monitoring.

Additionally, the wide-beam transducer will be useful in improving fetal monitoring in high risk obese subjects, which is generally difficult. The Corometrics transducer performed poorly during clinical testing on obese subjects resulting in the smallest average detection area.

Tables

TABLE 1

BMI Classifications

| BMI Category | Range | n |
|---|---|---|
| Underweight | <18.5 | 0 |
| Normal | 18.5-24.9 | 13 |
| Overweight | 25.0-29.9 | 10 |
| Obese | ≥30.0 | 3 |

BMI classifications and ranges as defined by the Center for Disease Control and Prevention and the number of subjects (n) which fall into each category.

TABLE 2

Effective coverage areas and percent increases

| BMI Category | BMI Value | Coverage Area, $cm^2$ Existing | Coverage Area, $cm^2$ Novel | % Increase | Mean Increase ± SD |
|---|---|---|---|---|---|
| Normal | 19 | 398.58 | 541.92 | 35.96 | 51.04 ± 38.0 |
| | 20 | 405.85 | 632.24 | 55.78 | |
| | 20.5 | 409.97 | 449.83 | 9.72 | |
| | 21.1 | 355.19 | 421.16 | 18.57 | |
| | 21.2 | 306.30 | 529.75 | 72.95 | |
| | 21.8 | 204.99 | 379.35 | 85.06 | |
| | 22.2 | 272.14 | 367.57 | 35.06 | |
| | 23 | 447.68 | 746.13 | 66.67 | |
| | 24 | 251.33 | 570.20 | 126.88 | |
| | 24 | 452.39 | 655.22 | 44.84 | |
| | 24 | 408.212 | 751.04 | 83.98 | |
| | 24.3 | 376.992 | 565.682 | 50.05 | |
| | 24.4 | 320.44 | 250.15 | -21.94 | |
| Overweight | 25.1 | 343.22 | 457.89 | 33.41 | 29.20 ± 11.3 |
| | 25.5 | 464.96 | 540.35 | 16.22 | |
| | 26.1 | 377.97 | 557.63 | 47.53 | |
| | 26.4 | 250.15 | 290.40 | 16.09 | |
| | 26.9 | 466.53 | 574.32 | 23.11 | |
| | 27.2 | 415.67 | 544.87 | 31.08 | |
| | 27.6 | 263.89 | 365.21 | 38.39 | |
| | 27.7 | 441.79 | 609.08 | 37.87 | |
| | 29.1 | 450.82 | 605.15 | 34.23 | |
| | 29.7 | 392.31 | 447.68 | 14.11 | |

TABLE 2-continued

Effective coverage areas and percent increases

| BMI Category | BMI Value | Coverage Area, cm² | | % Increase | Mean Increase ± SD |
|---|---|---|---|---|---|
| | | Existing | Novel | | |
| Obese | 33.4 | 206.17 | 631.46 | 206.29 | 98.07 ± 93.8 |
| | 37.3 | 367.17 | 513.06 | 39.73 | |
| | 43 | 432.75 | 641.28 | 48.19 | |

Shown are the effective coverage areas with the existing and novel transducers as well as the percent increases in each case for all subjects. Only one subject showed a decrease in effective coverage area with the novel transducer.

Relative to FIG. 7, there is shown an example diagram of the measurements taken on each subject. A-D corresponds to the existing Corometrics 5700 Ultrasonic transducer. A'-D' corresponds to the wide-beam ultrasonic transducer. Theoretical ellipsoidal areas comprised of the four quarter ellipsis (I-IV) are drawn. The origin and mediolateral and anteroposterior axes are labeled.

Figure 8:
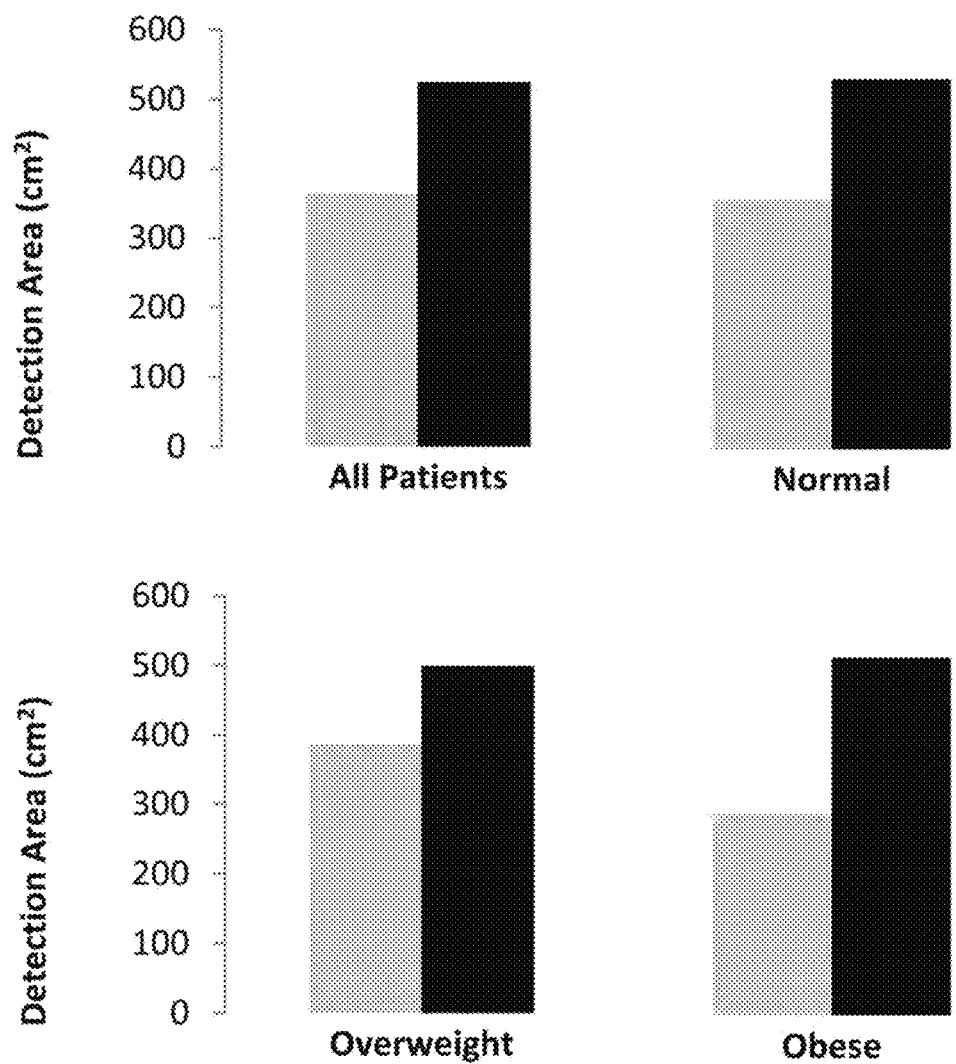
FIGS. 8 and 9 are sample data summarizing detection areas of various uterine probes.

There is illustrated with reference to FIG. 8 a comparison of the average detection areas for the existing Corometrics 5700 Ultrasonic transducer (left, grey bar) and the wide-beam transducer (right, black bar) for the entire subject sample (n=26), the normal BMI subgroup (n=13), the overweight sub group (n=10), and the obese subgroup (n=3).

Figure 9:
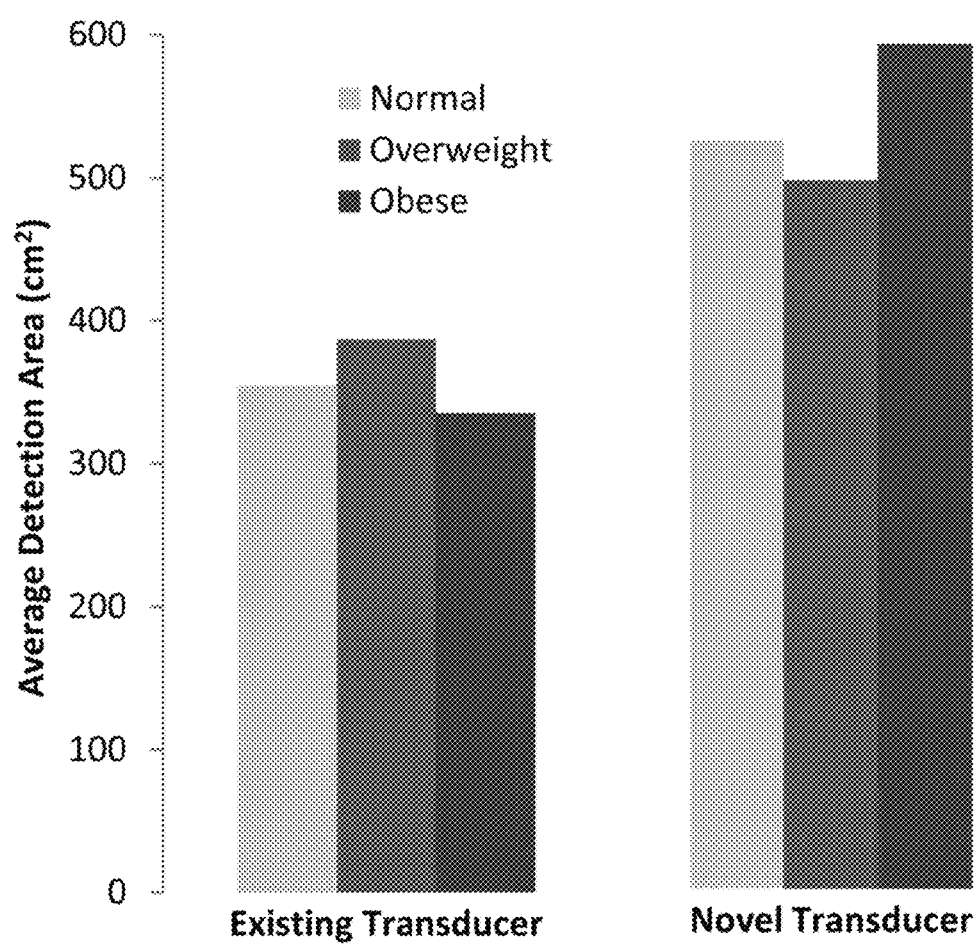

There is illustrated with reference to FIG. 9 a comparison of the average detection areas for the three BMI subgroups with the existing Corometrics 5700 Ultrasonic transducer and the wide-beam transducer. Normal BMI (light grey bar), Overweight BMI (dark grey bar), Obese BMI (black bar).

[End of Appendix A of U.S. Patent Application No. 61/457,087]

[Beginning of Appendix B of U.S. Patent Application No. 61/457,087]

[Beginning of Slide 1, Appendix B of U.S. Patent Application No. 61/457,087]

Figure 10:
FIG. 10 is a depiction of an ultrasound image.

Background
Fetal Heart Rate (FHR) Monitoring
Normal FHR=120-160 beats per minute
Early detection of fetal distress
Ability to closely monitor high risk patients
Uterine Contractions
Pregnancy period—Quiescent uterus, tight and rigid cervix
At term—Cervix dilation, vigorous contraction of the uterus
Pre-term birth—10% of pregnancies
Key to treatment
(FIG. 10 presented)
[End of Slide 1, Appendix B of U.S. Patent Application No. 61/475,087]

Figure 11:
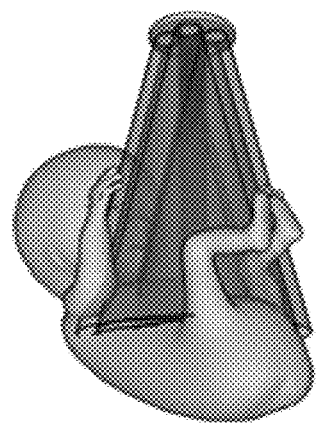
FIGS. 11 and 12 depict a multiple transducer probe having improved spatial detection, with FIG. 11 depicting a wide beam multiple transducer probe and FIG. 12 depicting a collimated beam multiple transducer probe.
Figure 12:
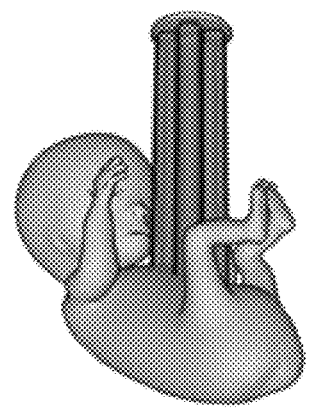
Figure 13:
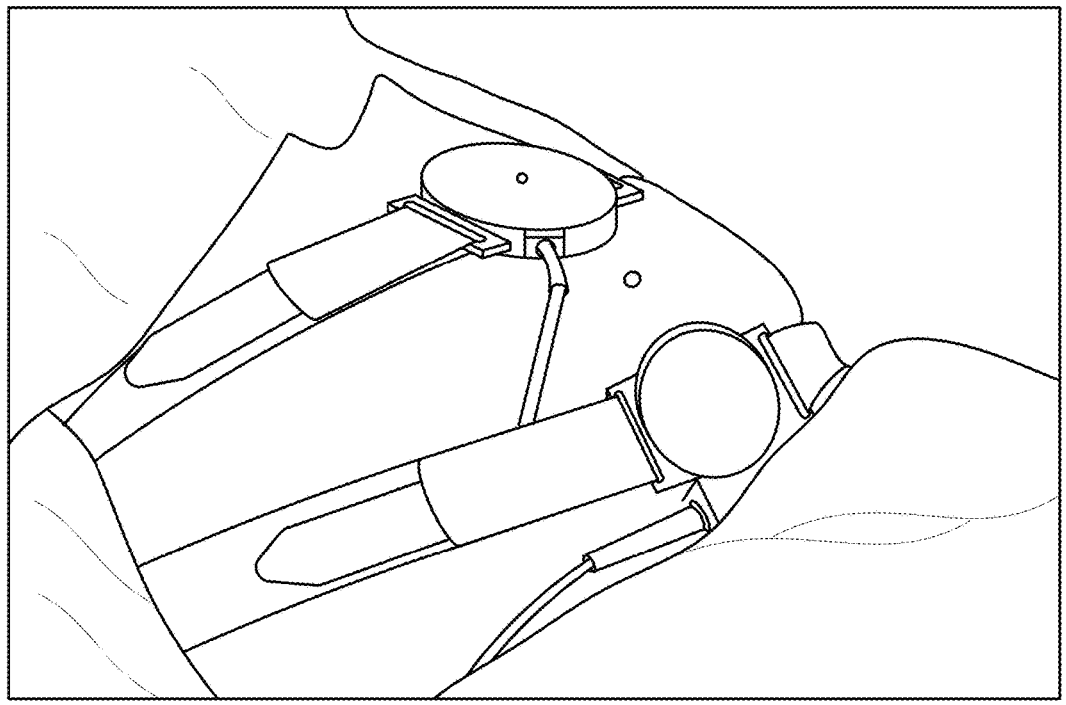
FIG. 13 is a depiction of a separate probes for fetal heart rate (FHR) detection and uterine contraction (UC) detection.

[Beginning of Slide 3, Appendix B of U.S. Patent Application No. 61/475,087]
Limitations of current devices
Low sensitivity
Restricted detection range
Immobilization of patient
Patient discomfort and distress
Invasive and indirect methods
With reference to FIGS. 11 and 12, there is illustrated multiple channel fetal heart rate monitoring ultrasound transducer with improved spatial detection and fetal tracking Our device works with commercial systems but provides 6 to 8 times the coverage area for heart rate detection. With reference to FIG. 13 there is illustrated an implementation of current technology.

[End of Slide 2, Appendix B of U.S. Patent Application No. 61/475,087]

Figure 14:
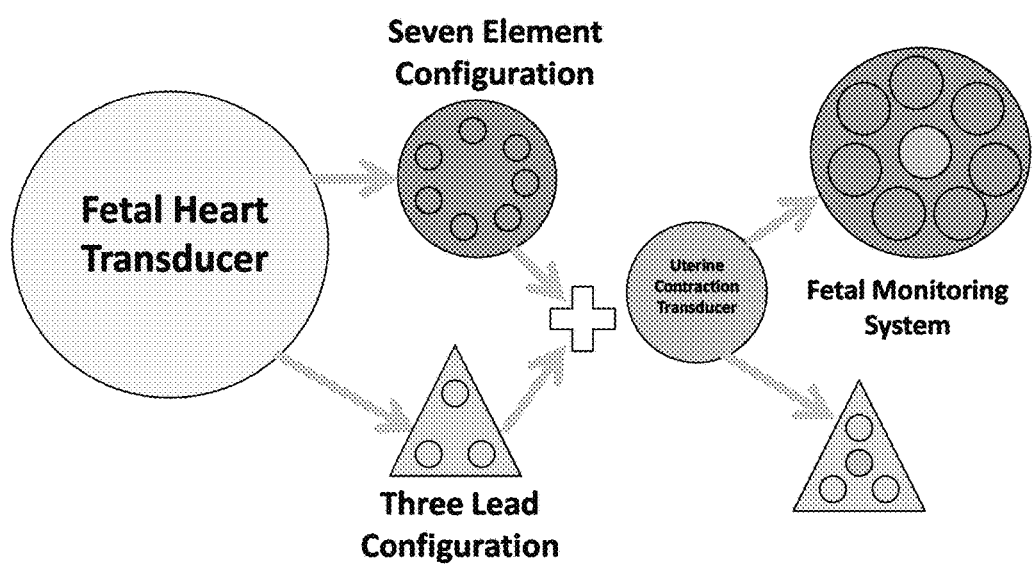
FIG. 14 is design overview diagram illustrating a multiple transducer uterine probe.

[Beginning of Slide 2, Appendix B of U.S. Patent Application No. 61/475,087]
With reference to FIG. 14 there is illustrated a new technology design overview.

[End of Slide 3, Appendix B of U.S. Patent Application No. 61/475,087]

Figure 15:
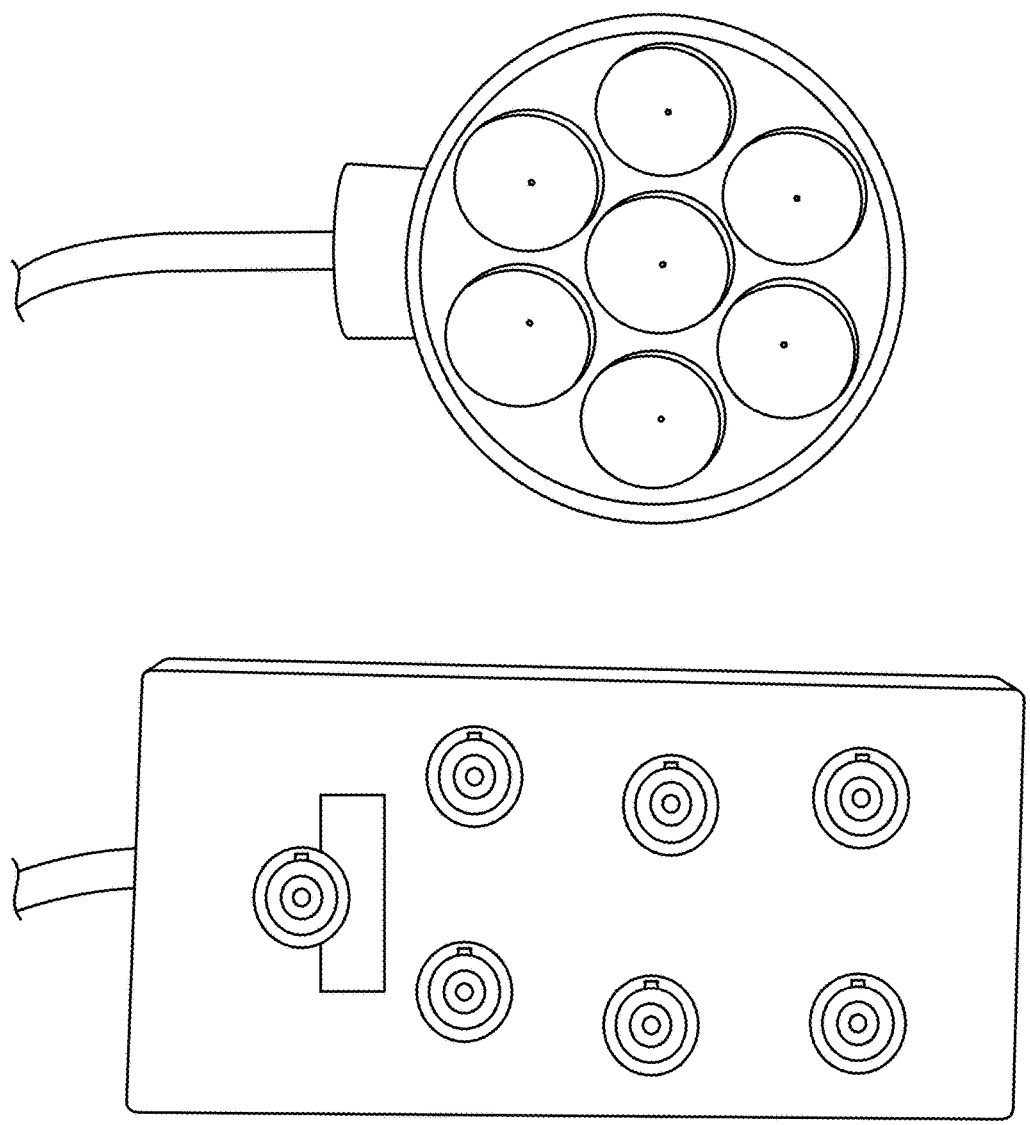
FIG. 15 is photographic image illustrating a multiple transducer uterine probe.

[Beginning of Slide 4, Appendix B of U.S. Patent Application No. 61/475,087]
New Technology
Novel Wide-beam Transducer
Wider beam to cover the entire area over which the fetus may shift
Wireless transducer
Can be used in conjunction with a wireless uterine device that can also measure strength of contractions for even greater coverage.
(FIG. 15 is referenced in connection with slide 4)
[End of Slide 4, Appendix B of U.S. Patent Application No. 61/475,087]

Figure 16:
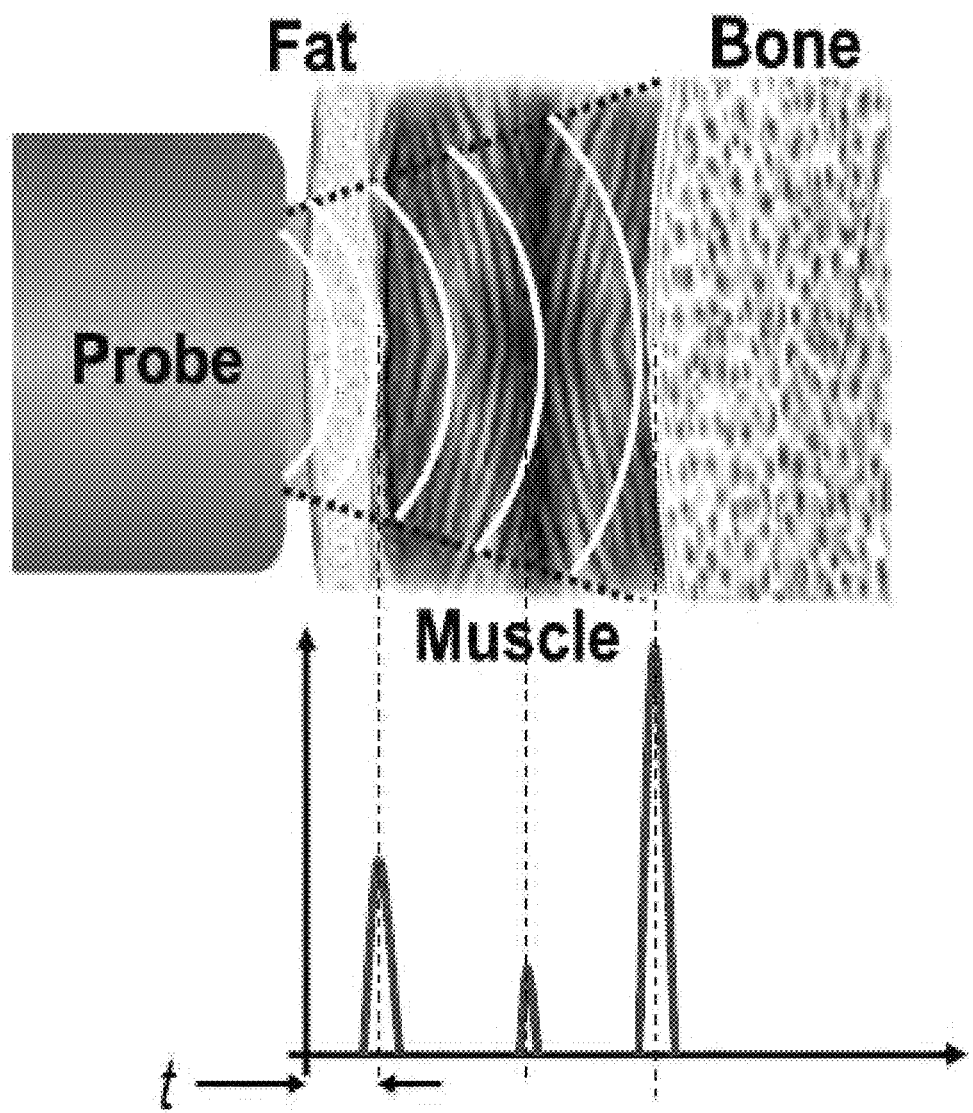
FIG. 16 is a depiction of signal representing an echo waveform reflected from uterine tissue barriers of a patient.

[Beginning of Slide 5, Appendix B of U.S. Patent Application No. 61/475,087]
Ultrasound imaging physics
Fetal heart monitor (FHM)—employs Doppler ultrasound.
Uses high frequency sound waves and their echoes to obtain images.
The sound waves travel are strongly reflected at the tissue interfaces (fat-muscle, or muscle-bone).
Images are formed by recording the reflected sound echoes.
The distance between echoes corresponds to the contraction duration and amplitude, the strength.
(FIG. 16 is referenced in connection with slide 5)
[End of slide 5, Appendix B of U.S. Patent Application No. 61/475,087]

Figure 17:
FIG. 17 is a depiction of uterine tissue boundaries.

[Beginning of Slide 6, Appendix B of U.S. Patent Application No. 61/475,087]
In relation to reference element 1601 of FIG. 17, there is illustrated a skin and fat layer interface.
In relation to reference element 1602, there is illustrated muscle layer in a relaxed state.
In relation to reference element 1603, there is illustrated a contracted muscle-bone interface.
In relation to FIG. 18, there is illustrated an analyzed waveform.
In relation to element 1701, Y-axis is signal amplitude, high spikes are observed at tissue boundaries.
In relation to element 1702, generally first large spike is fat-muscle boundary.
In relation to element 1703, spikes between fat-muscle and muscle-bone boundary are caused by tissue structure. Fatty muscle shows more spikes than lean muscle. Fascia, veins, arteries can also produce spikes.
In relation to element 1704, last large spike is muscle-bone boundary.
[End of Slide 6, Appendix B of U.S. Patent Application No. 61/475,087]

Figure 19:
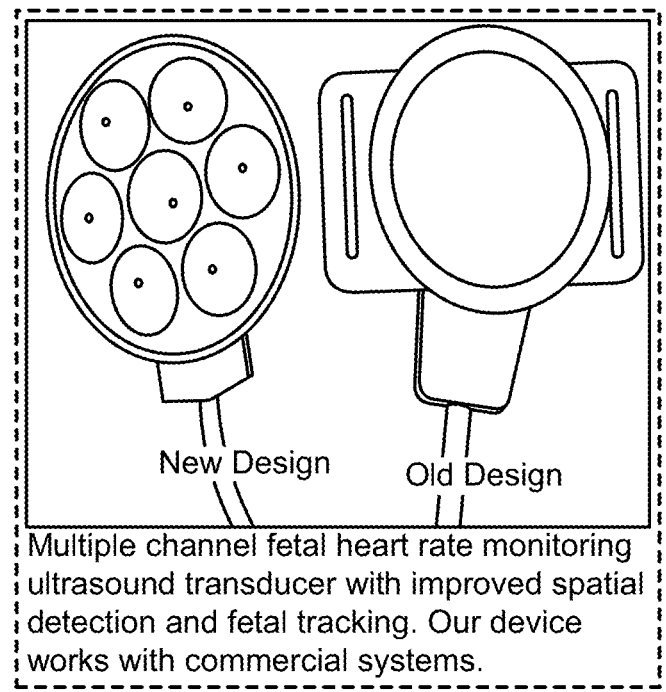
FIG. 19 is a photographic depiction of a multiple transducer probe in which multiple transducers are disposed in fixed relative spatial relation.

[Beginning of Slide 7, Appendix B of U.S. Patent Application No. 61/475,087]
Wide-bean transducer design.
With reference to FIG. 19, there is illustrated seven element configuration.

Figure 20:
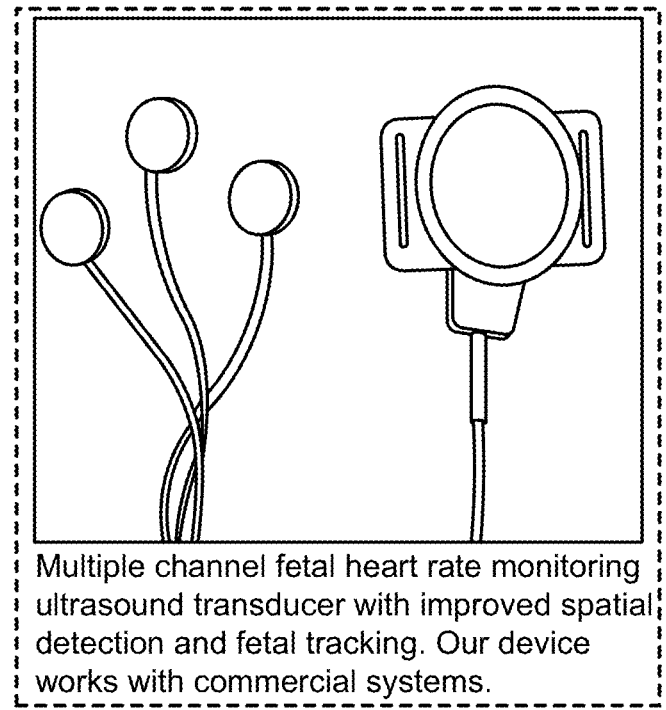
FIG. 20 is a photographic depiction of a multiple transducer probe in which multiple transducers are disposed in variable relative spatial relation.

With reference to FIG. 20, there is illustrated multiple channel fetal heart rate monitoring ultrasound transducer with improved spatial detection and fetal tracking Our device works with commercial systems.

With reference to FIG. 20, there is illustrated three lead configuration.

With reference to FIG. 20, there is illustrated multiple channel fetal heart rate monitoring ultrasound transducer with improved spatial detection and fetal tracking Our device works with commercial systems.

[End of Slide 7, Appendix B of U.S. Patent Application No. 61/475,087]

[Beginning of Slide 8, Appendix B, U.S. Patent Application No. 61/475,087]

Figure 21:
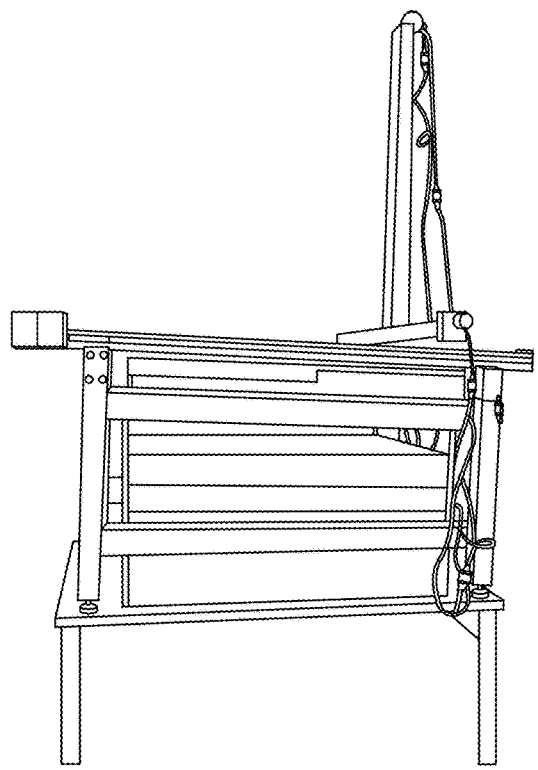
FIGS. 21 and 22 are depictions of an ultrasound beam scanning system.
Figure 22:
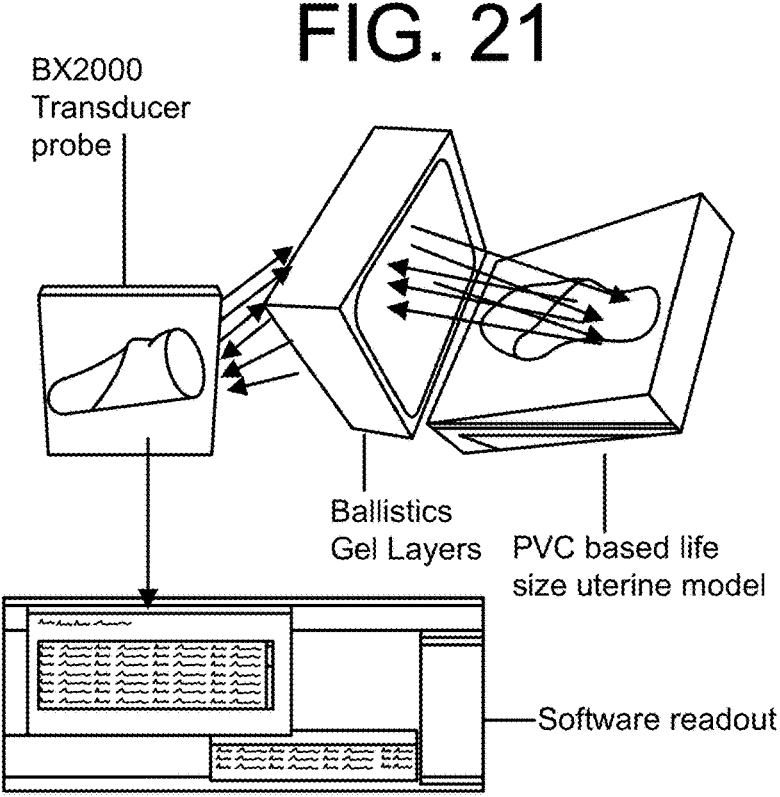

Phantom heart model
3D ultrasound beam scanning system
Measure ultrasound fields
Simulate fetal heart in vitro
(FIGS. 21 and 22 are referenced with slide 8)

[End of Slide 8, Appendix B of U.S. Patent Application No. 61/475,087]

[Beginning of Slide 9, Appendix B of U.S. Patent Application No. 61/475,087]

Results

Figure 23:
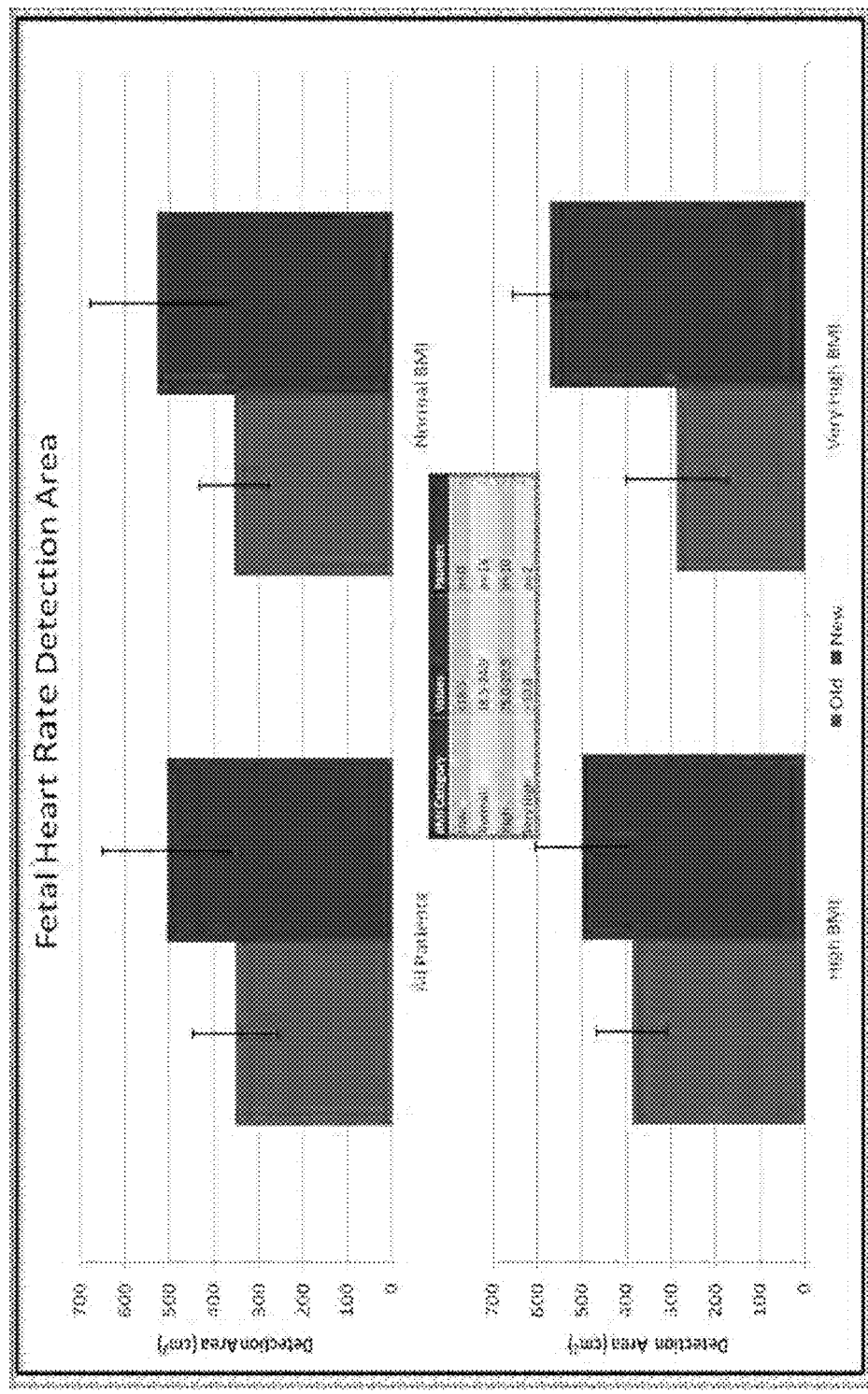
FIG. 23 is a graphical depiction of a comparison between probes relative to a fetal heart rate detection area.

With reference to the data of FIG. 23, average fetal heart beat detection areas for a current ultrasound transducer ('old') and the novel wide beam transducer ('new') grouped by the patient sample and BMI subgroups. Error bars indicate standard deviation.

[End of Slide 9, Appendix B of U.S. Patent Application No. 61/475,087]

[Beginning of Slide 10, Appendix B of U.S. Patent Application No. 61/475,087]

Results

The novel wide-beam transducer consistently performed better than the current transducers.

The detection area was greater with the new transducer for 24 out of 25 patients.

Total detection areas were found to be significantly different ($p<0.001$) for the entire patient sample.

The detection area was smallest for high BMI patients with the old transducer and largest for high BMI patients with the new transducer.

[End of Slide 10, Appendix B of U.S. Patent Application No. 61/475,087]

[End of Appendix B of U.S. Patent Application No. 61/475,087]

[End of U.S. Patent Application No. 61/475,087]

In connection with FIG. 6 it was described that each of a plurality of transducer elements (transducers), e.g., a first transducer and a second transducer, can have an associated lens 13 for use in forming a conical beam. The configuration of FIG. 6 provides a wide area coverage of a target with minimal holes in the coverage. With a lens per transducer arrangement as set forth in FIG. 6 there will be provided a conical beam for each lens transducer pair. Each transducer and lens pair can have an individual acoustic beam. Lens 13 can be regarded as an acoustical lens. Lens 13 can comprise a material that can transmit sound, e.g., acrylic or glass. Each lens 13 can have an index of refraction of and a radius of curvature.

Figure 25:
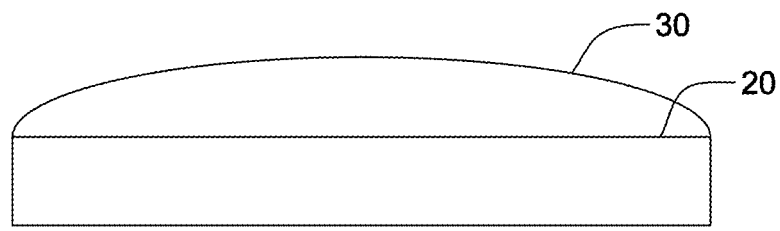
FIG. 25 is a depiction of a transducer having an associated acoustic lens.

In FIG. 24 there are shown various embodiments of a uterine probe, in each of several configurations, "A" through "E". Probe 10 can have one to N transducers 20. In the configurations "A"-"E" as depicted in FIG. 24, transducers 20 can be disposed to be in fixed relative positions, e.g., on a carrier external to transducers 20, as depicted with reference to the various configurations. Features as set forth in connection with FIGS. 2 through 6 herein can be incorporated in any one of probes "A"-"E". In one embodiment a probe 10 of any one of configurations "A"-"E" can have both angled mountings of transducers so that a line is perpendicular to respective active surface of first and second (and possibly third and fourth, etc.) transducers 20 are non perpendicular to one another and further so that first and second (and possibly third and fourth, etc.) transducer 20 have an associated acoustic lens 30 (labeled element 13 in FIG. 6). Transducers 20 depicted in FIG. 20 are labeled to indicate a generic functionality of the transducers, e.g., a transducer 20 here can be adapted for use in one or more of FHR detection, uterine contraction detection and can be responsive to generic energy input, e.g., sound, light, force. As depicted in FIG. 25 each transducer 20 can be provided with an associated acoustic lens 30. Alternatively, each transducer 20 can be devoid of lens 30. In some embodiments, some transducers are provided with associated lens 30 and some transducers 20 are provided without associated lens 30. One or more, and in one embodiment, each transducer 20 of probe 10 can be provided by a piezoelectric element, e.g., a lead zirconate titanate (PZT) transducer.

Figure 26:
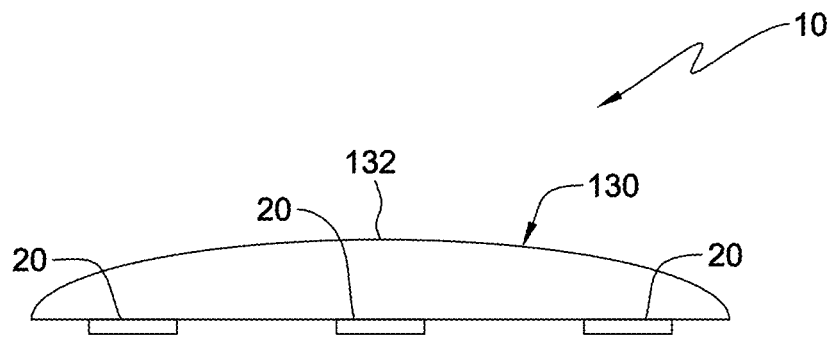
FIG. 26 is a depiction of a multiple transducer probe having a multiple transducer probe having a monolithic lens for shaping sound waves emitted from each of several different transducers.

In another embodiment as shown in FIG. 26 probe 10 can include a monolithic acoustic lens 130 having a radius of curvature and a single apex 132 for probe 10. As shown in FIG. 26 monolithic acoustical lens 130 can be disposed acoustically forwardly of each of a plurality of probes and can shape sound waves of each of a plurality of transducers. In some applications the embodiment of FIG. 26 can be advantageous; notably in some embodiments providing certain cost and ease of manufacture advantages.

However in one aspect the providing of acoustical lens 30 on a one per transducer basis can provide numerous advantages. For example, the configuration as shown in FIG. 6 with a different acoustical lenses 13 provided for each of first, second third and fourth fifth sixth and seventh transducers can provide improved uniformity of an acoustical field. Referring to the embodiment of FIG. 26 monolithic lens 130 can be expected to substantially image a source plane into target space. To the extent the source plane includes gaps defined by spaces between transducers such gaps can be expected to be imaged into target space. With a diverging lenses the gaps can be expected to be made larger as the field depth increases. Accordingly, a target within the outer boundaries in an imaged area, e.g., a fetus can go undetected if located within a void during use of probe 10 for detecting.

The configuration as shown in FIG. 6 allows holes or gaps to be filled readily by proper configuring of an acoustical lens for each of several transducers. Reduction of gaps in a target space can be further facilitated with use of a configuration as shown in FIG. 6 wherein first and second transducers are disposed at angles so the imaging axis 14 of each of first and second and third transducers are non-parallel to one another.

Figure 27:
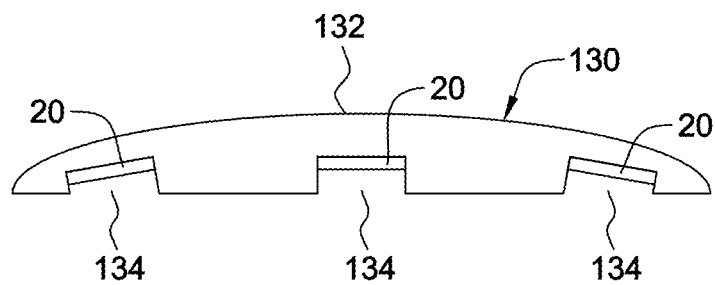
FIG. 27 is a depiction of a monolithic lens having a plurality of formations for orienting each of several transducers.

While the embodiment of FIG. 26 can exhibit holes or voids in a detection space, hole reduction can be facilitated by angling of transducers 20 to be non-parallel. In the embodiment of FIG. 27 a sound entry surface of lens 130 can have orientation aiding formations 134 for orienting transducers 20 to include non-parallel imaging axes. While FIG. 27 shows a cross sectional side view it will be understood that the arrangement of FIG. 27 can provide light shaping wherein transducers 20 from a top view are disposed over a two dimensional area as shown by configurations C through E of FIG. 24. The orientation aiding features of FIG. 27 can be applied to any of the configurations as shown in Fig. C through E of FIG. 24 so that each transducer 20 of the configuration is oriented by lens 130 to the end that a line extending perpendicularly through an active (front face) surface of the transducer is non-parallel to a line extending perpendicularly through an active surface of each other transducer. In such manner first, second and third transducers disposed over a two dimensional area from a top view perspective have different orientations as determined by lens 130. Lines extending perpendicularly through a surface of transducers 20 can be non-parallel.

Still referring to advantages of a configuration as shown in FIG. 6 having a first lens for a first transducer and a second lens for a second transducer the configuration can improve acoustic coupling with a patient. Referring to the embodiment of FIG. 26 it is seen that acoustic coupling can be possibly challenging since apex 132 of the convex lens surface of lens 130 must be coupled to an apex of another surface, namely a patient's stomach which defines an opposing convex apex. The configuration as set forth in FIG. 6 can have a generally flat distal end. The generally flat distal end can have lenses defining one or more apex, but with the one or more apexes of lesser height than apex 132. With the configuration of FIG. 6 the distal end of probe 10 can be configured to provide good contact with a patient's stomach.

In one embodiment each transducer 20 of probe 10 can have an associated lens 30 except for center transducer, e.g., transducer 20 at location "h" of configuration D or location "n" of configuration E, FIG. 24. In such an embodiment the center transducer can be used solely or on a priority basis in a UC signaling configuration and the remaining transducers can be operated solely or on a priority basis in an FHR signaling configuration. In such an arrangement a distal end of probe 10 can be generally concave to promote good acoustic coupling. The center transducer can emit collimated beams and the remaining transducers can emit conical or otherwise diverging beams, as shaped by their respective lenses.

With the configuration of FIG. 6 being devoid of a monolithic lens apex, a distal end of probe 10 can be made larger, a detection area of probe 10 can be made larger than would be possible with use of a monolithic lens. A detection area provided by probe 10 can therefore be increased. Notably, with a larger diameter probe, a detection area in the near field (closer to the stomach surface) can be increased.

Figure 28:
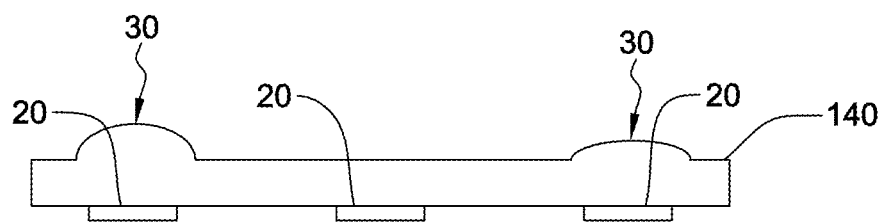
FIG. 28 is a cross sectional side view of a unitary material member that defines a plurality of acoustic lenses.

While the plurality of lenses in the embodiment of FIG. 6 are shown as being provided by different material members, the plural acoustic lenses as shown in FIG. 6 can also be formed of a common material member, e.g., a unitary material member that defines a different lens for each of first and sense transducers and in one embodiment each of N transducers of a probe. Such a unitary material member 140 that defines first and second lenses 30 for first and second transducers 20 is shown in FIG. 28. In the embodiment of FIG. 28 the lenses for respective transducers can be of the same size (e.g., same radius of curvature) or can be of different sizes as shown. The first and second lenses can be of the same or different lens types, e.g., one can be spherical and one can be cylindrical depending on the design requirements of the emitted beam profile. With reference to FIG. 28 there is shown a defined distal end of a probe 10 that is generally concave in shape where the cross section is repeated radially for a probe 10. The general concavity is defined by lenses 30 at a periphery extending more extensively than a central region of the probe distal end indicated by FIG. 28. The providing of a concave shape for a distal end of probe 10 can be facilitated by providing a center transducer 20 to be devoid of an associated lens 30, as indicated by FIG. 28. A center transducer can emit a collimated beam while peripheral transducers can emit conical or otherwise diverging beams as shaped by their associated lenses. A concave shape for a probe distal end can promote good acoustic coupling. While FIG. 28 shows a cross sectional side view it will be understood that the arrangement of FIG. 28 can provide light shaping wherein transducers 20 from a top view are disposed over a two dimensional area as shown by configurations C through E of FIG. 24. The light shaping features of FIG. 28 can be applied to any of the configurations as shown in Fig. C through E of FIG. 24. In such manner first, second and third transducers disposed over a two dimensional area from a top view perspective can be shaped by respective first second and third lenses that are defined in a common material member. In one embodiment as shown in FIG. 6 probe 10 can include a carrier that angles imaging axes of each of several transducers 12 so that they are in diverging relation.

As noted, the configuration wherein a plurality of lenses are provided on a one to one basis (there being a lens provided per each transducer) allows a distal end of probe 10 to be generally flat and accordingly, increases a maximum diameter to which a distal end of probe 10 can be constructed while still achieving good acoustic coupling. In one embodiment a diameter of a distal end of probe 10 can be greater than 5.0 cm and in one embodiment greater than 6.0 cm, e.g. 6.7 cm, and in one embodiment greater than 9.0 cm, e.g., 10.0 cm. In one embodiment a diameter of a distal end of probe 10 can be greater than or less than 1.0 cm. Increasing a diameter of a distal end of probe 10 brings transducers of probe 10 closer to an area being detected and accordingly can improve a signal to noise ratio of probe 10. While in some applications increased diameter of probe 10 can be advantageous (e.g., for optimized near field detection) in other applications, such as applications where probe 10 is to be worn by a patient, a decreased diameter of probe 10 can be advantageous.

Referring to FIG. 7 a detection profile of probe 10 can be configured to shaped in accordance with a woman's natural anatomy. Referring to FIG. 6 detection profile has a wider width and than height and is generally oval in shape. The detection range along a mediolateral axis is greater than a detection range or air anteroposterior axis is the example of FIG. 7. In the development of probe 10 it was determined that detection areas of commercially available probes can include a circular configuration and accordingly are not matched to a woman's anatomy. The shaping of a detection area to a woman's natural anatomy decrease a likelihood of a fetus moving to an area outside of a detection area of probe 10, and also decreases power consumption, as well as reduces unwanted sound wave exposure.

In another aspect, probe 10 can emit an arrangement of beams, a beam profile to correspond to a defined detection area wherein the detection area is asymmetrical and corresponds to physiological limits on a detection area that are imposed by asymmetrical attributes of a patient's body. Matching a beam projection profile to a patient's body provides significant advantages including reduction of power consumption and reduction of unwanted beam exposures.

Figure 29:
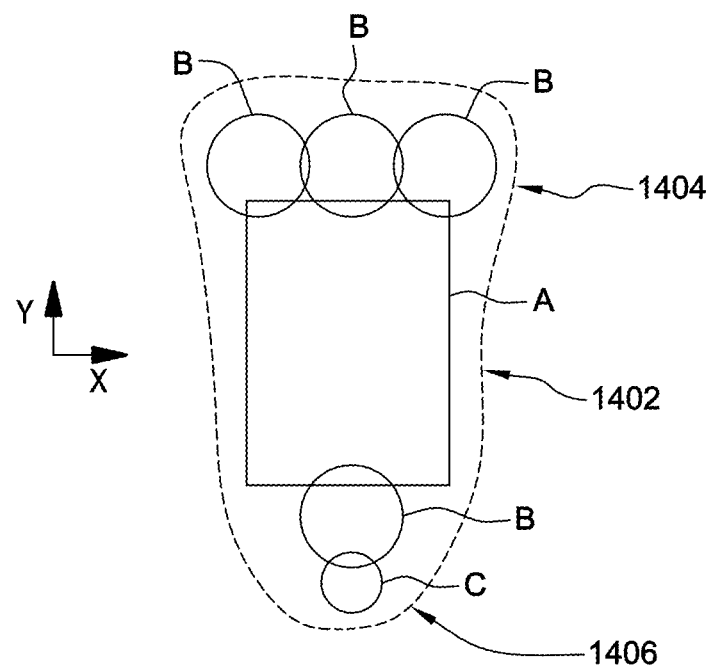
FIG. 29 is a schematic diagram illustrating an asymmetrical physiologically determined detection area and a corresponding emission profile.

In one embodiment, a beam profile of probe 10 is established to coincide with a detection area delimited in accordance with physiological attributes of a patient's body as determined using patient test data, as illustrated in FIG. 1. In another embodiment, a beam profile is established to coincide with a detection area as defined by known physiological attributes of an average patient's body. In FIG. 29 there is a depicted an asymmetrical detection area 1402 as delimited by a known shape of a patient's detection area and including generally a uterus area 1404 combined with a vaginal canal area 1406. Detection area 1402 is asymmetrical as it is asymmetrical along the Y axis depicted. In another embodiment, a detection area can be regarded as being asymmetrical for being asymmetrical just along the X axis or along both the X axis and Y axis. In the example of FIG. 29 beams are projected generally in a Z axis direction.

Figure 30:
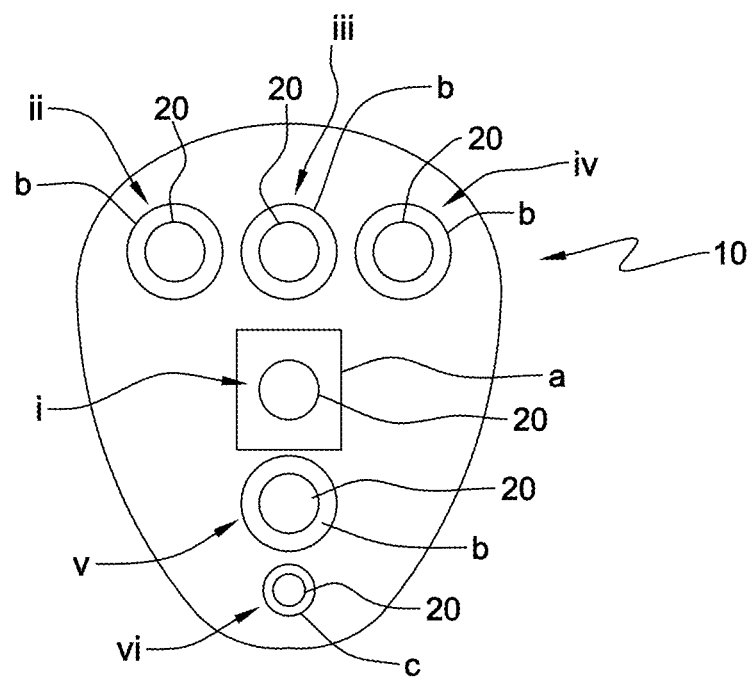
FIG. 30 is a schematic diagram of a probe having a transducer and optics arrangement that configure the probe for emission of an asymmetrical beam profile that corresponds to a physiologically determined detection area.

As indicated in connection with FIG. 30, probe 10 can be configured to project an arrangement of beams to coincide with detection area 1402. In one embodiment, probe 10 for purposes of projecting an asymmetrical beam profile can include lenses of different types (e.g. spherical and cylindrical) and or different sizes. Various cross sections of beams are depicted in FIG. 29. Rectangular beam cross section (beam) A can be projected with use of a cylindrical lens "a", circular beam cross section B can be projected with use of a spherical lens "b" of a first relatively larger size and circular beam cross section C can be projected with use of a spherical lens "c" of a second relatively smaller size. A probe 10 for projecting the beam profile as depicted in FIG. 29 is depicted in FIG. 30. In the embodiment of FIG. 30, transducer 20 at location i includes an associated cylindrical acoustic lens "a" for projection of beam A, transducers 20 at locations ii, iii, iv, and v having relatively larger spherical lenses "b" for projection of beams B, and transducer 20 at location vi having a relatively smaller spherical lens c for projection of beam c. The transducer sizes and relative positions can also be arranged in asymmetrical pattern for facilitation of a beam profile to coincide with an asymmetrical detection area such as detection area 1402 depicted in FIG. 29.

In connection with FIG. 3 there are described probes having a plurality of transducers. In one embodiment, the probes can have transducers for use in detecting fetal heart rate. In one embodiment, the probes can have transducers for use in detecting uterine contractions. In one embodiment transducers of the probe can be of a different technologies. In another embodiment, the transducers of probe 10 can be of a common technology. For example, in the embodiment of FIG. 3 it was described that a probe 10 can have a transducer 12 for fetal heart rate monitoring and a transducer 22 for uterine contraction monitoring that are co-located.

As indicated in FIG. 3, probe 10 can include a certain transducer, e.g., co-located transducer 12, 22 for use in detecting both fetal heart rate and uterine contractions. A transducer labeled reference element 20 herein e.g., transducer 20 in any one of configuration "A" through "E" of FIG. 24 can in the manner of transducer 12, 22 as shown in FIG. 3, be used in one or more signaling configuration, e.g., a fetal heart rate (FHR) signaling configuration and a uterine contraction (UC) signaling configuration. In such an embodiment, a certain transducer 20, e.g., any one of transducers 20 can be driven in both a FHR signaling configuration and a uterine contraction (UC) configuration. With reference to FIG. 24 there are illustrated various configurations "A" through "E" of probes 10 which can have one or more transducer operative in one or more signaling configuration.

Figure 31:
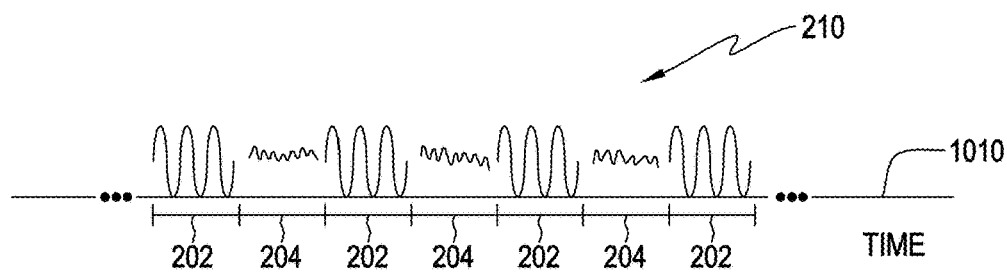
FIG. 31 is a timing diagram depicting operation of a transducer operating to intermittently emit and detect sound waves for detection of a fetal heart rate (FHR)

In reference to timing diagram of FIG. 31 there is illustrated operation of a transducer 20 operative for detection of a fetal heart rate. For FHR monitoring, transducer 20 can emit a burst wave during emit periods 202. The burst wave signal can comprise a plurality of cycles, on the order of tens of cycles, e.g. 50 cycles, at a known frequency, e.g., 1-3 MHz. Emit periods 202 can be followed by detection periods 204. During detection periods 204 transducer 20 receives an echo signal which can be processed for detection of a fetal heart rate e.g., by monitoring unit 100. Doppler FHR monitoring can comprise (a) emission of an ultrasonic burst comprising multiple cycles, (b) recording a frequency and/or phase shifted "echo" signal waveform, (c) processing the waveform to determine a "Doppler Shift", and (d) repeating (a) through (c) a plurality of times. A fetal heart rate can be determined based on a frequency shift in an echo waveform resulting from motion of a heart. FHR monitoring can be performed so that there are on the order about ten (10) detection periods per heart beat. A reflected echo waveform will be Doppler shifted during the course of a heart beat. As the wave moves through tissue, it can be reflected back to a receiver on the transducer. Movement in the tissue will alter the frequency of the reflected wave (Doppler shift) and this change will be detected by system 1000.

FIG. 31 depicts pulse wave Doppler operation, which can be alternatively termed intermittent wave Doppler wave. In accordance with intermittent wave Doppler operation probe 10 can emits waves at specific bursts, and the time between bursts is used to receive any reflected waves. The timing of the bursts allows for a process called range gating. Essentially, the bursts and receiving periods can be timed such that only motion in a predetermined sample volume will be detected, allowing interfering information to be ignored. Additionally, pulse wave ultrasound reduces the overall exposure of the patient to ultrasound waves.

Figure 32:
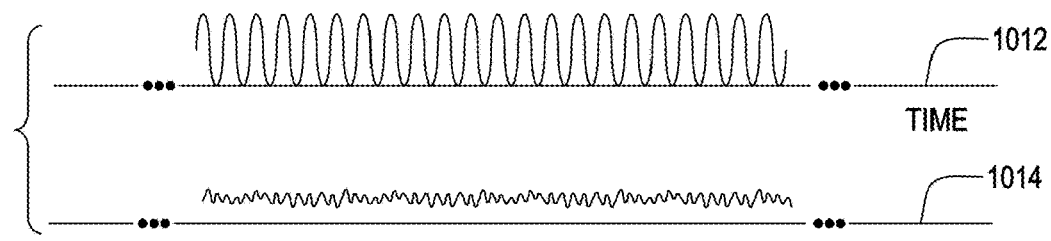
FIG. 32 is a timing diagram depicting operation of a first transducer operative to continuously emit sound waves and a second transducer operative to continuously detect emitted sound waves reflected from a target for detection of a fetal heart rate (FHR)

A certain transducer 20 of probe 10 can also operate in accordance with continuous wave Doppler operation. In accordance with continuous Doppler operation as depicted by FIG. 32, probe 10 can emit continuous ultrasound waves at a known frequency (usually 1-3 MHz). As the wave moves through tissue, it can be reflected back to a receiver on the transducer. Movement in the tissue will alter the frequency of the reflected wave (Doppler shift) and this change will be detected by the transducer and monitoring unit. An FHR signaling configuration for transducer 20 is depicted by timeline 1010 of the timing diagram of FIG. 31 (emitting and detecting) and timeline 1012 of FIG. 32 (emitting), and timeline 1014 of FIG. 32 (detecting).

Figure 33:
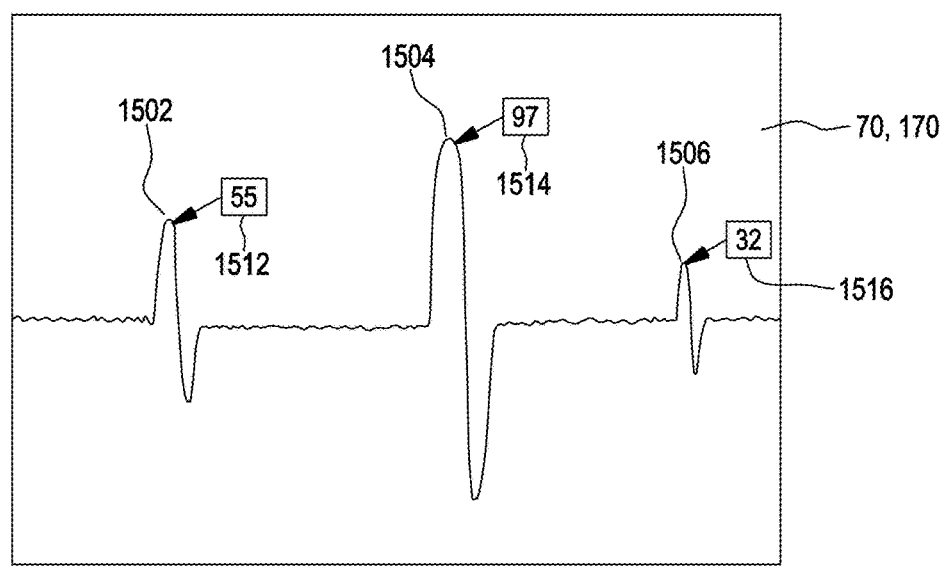
FIG. 33 is depiction of a user interface display that displays a continually updated line graph that simulates an output of a commercially available mechanical based contraction detector.

In connection with FIG. 16 it was described herein that probe 10 can have a transducer 22 that can emit and detect acoustic waves for use in monitoring uterine contractions. An output by a system 1000 detecting uterine contractions is depicted in FIG. 33. A probe emitting acoustic waves for detection of uterine contractions is illustrated with reference to the timing diagram of FIG. 34. At periods 302, which can be termed emission periods transducer 20 can emit a pulse waveform. The pulse waveform can comprise a fewer number of cycles than a waveform for use in FHR detection. In one example the number of cycles is less than five cycles, e.g., one to two cycles where as the waveform for use in FHR detection can comprise tens of cycles, e.g., 20, 30, 40 or 50 cycles. The pulse waveform can be emitted at a known frequency (e.g., 1-3 MHz). At periods 304, transducer 20 can be detecting an echo signal received from body tissue. As indicated in FIGS. 15 and 23 an echo signal can comprise a plurality of peaks. The distance between the peaks correspond to the contraction duration and amplitude, the strength. A series of echo signals (signals of a succession of sampling periods) can be processed for determination of when a contraction is occurring.

Figure 18:
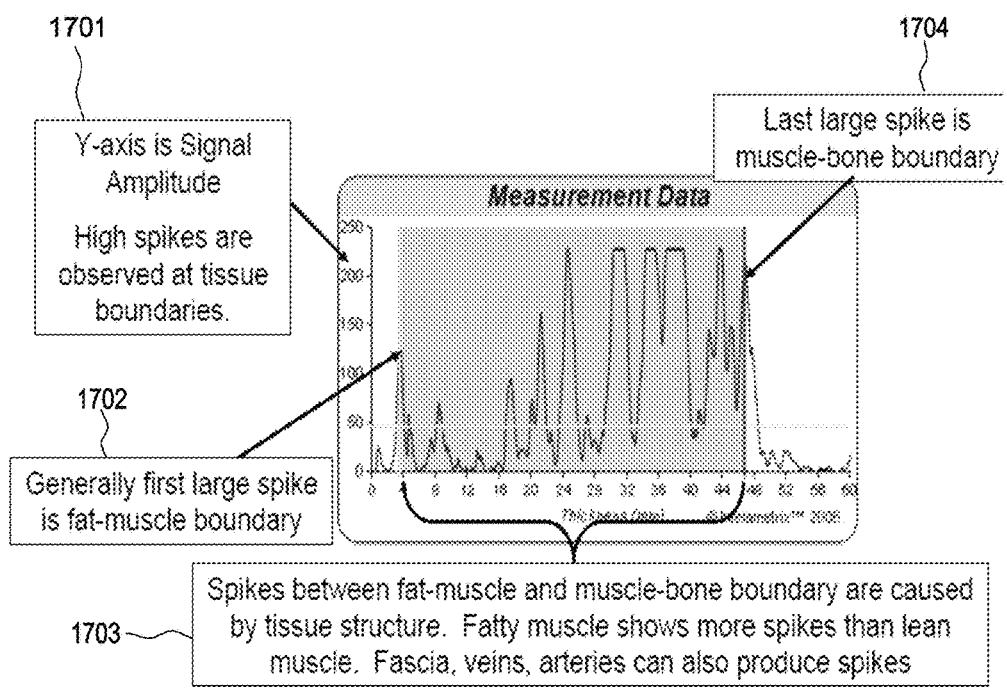
FIG. 18 is a depiction of signal representing an echo waveform reflected from uterine tissue barriers of a patient.

Contractions can be profiled by examining echoes over one or more detection periods. Referring to the echo waveform of FIG. 16 and FIG. 18, peaks of an echo waveform correspond to tissue interfaces, e.g. fat to muscle, muscle to muscle, muscle to bone. During a contraction, peaks of an echo waveform can change position in time as a result of a muscle movement. During a uterine contraction, a plurality of peaks corresponding to tissue interfaces as shown in FIGS. 16 and 18 can be expected to shift by a determinable amount of time with reference to a reference time (the position in time of a set of peaks in the absence of a contraction) over a sequence of detection periods and then return to normal state. A strength of a contraction can be determined based on the magnitude of time shift between a first set of peaks (at a first time) representing tissue interfaces in a normal state and a second set of peaks (at a second time after the first time) representing the tissue interfaces in a contracted state and the elapsed time (the speed) between the first time and the second time. The elapsed time can be determined based on the number of detection periods. In one embodiment, system 1000 can process the echo signal and present for display on a user interface display of system 1000, e.g., user interface 70 and/or 170 continuously updated line graph 1500 wherein a uterine contraction is depicted as one or more "peak" in the line graph. The described output simulates an output of a commercially available contraction detector wherein strength of a contraction is measured responsively to an output of a mechanical force sensor. Referring to FIG. 33, peaks 1502, 1504, 1506, can be displayed with relative amplitudes corresponding to a measured strength of a contraction. Numerical values 1512, 1514, 1516 indicative of uterine contraction strength can also be presented on a user interface display, e.g. user interface 70 and/or 170. In one embodiment, a processing of a waveform by system 1000 detected with use of a transducer 20 operating in an FHR signaling configuration can include examining sound waveform representing signals for frequency shifts. A processing of a waveform by system 1000 detected with use of a transducer 20 operating in a UC signaling configuration can include examining sound waveform representing signals for time shifts.

Figure 34:
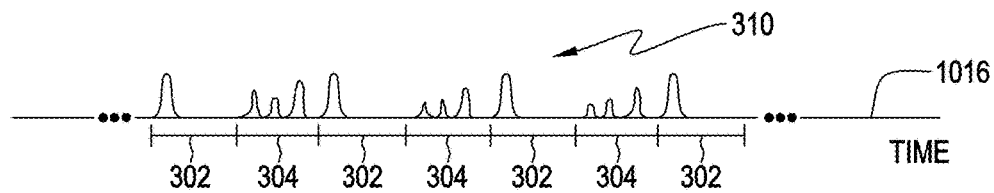
FIG. 34 is a timing diagram depicting operation of a transducer operating to intermittently emit and detect sound waves for detection of a uterine contraction (UC)

FIG. 34 depicts intermittent wave UC detection operation. In accordance with intermittent wave UC detection operation probe 10 can emit waves at specific bursts, and the time between bursts is used to receive any reflected waves. The timing of the bursts allows for a process called range gating. Essentially, the bursts and receiving periods can be timed such that only motion in a predetermined sample volume will be detected, allowing interfering information to be ignored. Additionally, intermittent wave ultrasound reduces the overall exposure of the patient to ultrasound waves.

Figure 35:
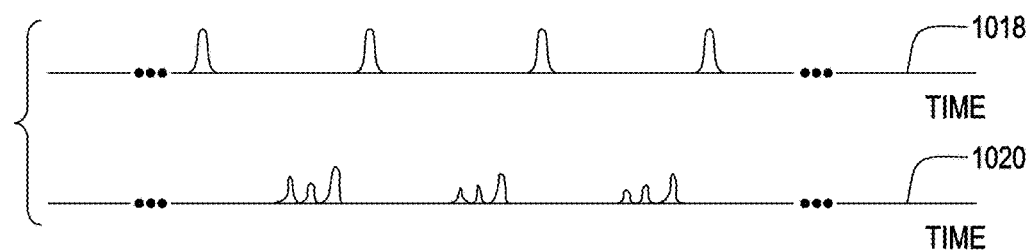
FIG. 35 is a timing diagram depicting operation of a first transducer operative to continuously emit sound waves and a second transducer operative to continuously detect emitted sound waves reflected from a target for detection of a uterine contraction (UC)

FIG. 35 illustrates continuous wave UC detection operation. In the embodiment of FIG. 35 a first transducer having operation depicted by timeline 1018 can continually emit pulse waveform for detection of a uterine contraction parameter without entering a detection period. A second transducer having an operation depicted by timeline 1020 can be employed for detection of the emitted sound wave as reflected from a tissue interface. A second transducer having operation depicted by timeline 1020 can be detecting reflected sound waves concurrently while a first transducer having operation depicted by timeline 1018 emits sound waves. A UC signaling configuration for a transducer is depicted by timeline 1016 (intermittent emit and detect), timeline 1018 (continuous emit) and timeline 1020 (continuous detect).

In the embodiments depicted with reference to the timing diagrams of FIGS. 34 and 35 uterine contraction detection can be accomplished by emitting sound waves and processing signals representing reflected sound waves. In one embodiment, a transducer 20 of probe 10 for measuring a contraction can be a transducer responsive to a mechanical force applied thereto. Incorporating a mechanical force sensor in probe 10 can be useful in certain embodiments. Where a transducer is employed that detects contraction parameters utilizing sound waves as set forth herein, the contraction information is a direct measurement of the tissue movement that defines the contraction. In the case of a mechanical force detector, the detector signal is not a direct measurement of tissue movement defining the contraction but rather an indirect measurement of contraction measured by way of force transference through body tissue members.

In the embodiments as described in connection with the timing diagrams of FIGS. 31 and 34 detection periods can follow emission periods. In another embodiment, as described in connection with timing diagram of FIG. 32 and the timing diagram of FIG. 34, probe 10 can have a plurality of transducers and probe 10 can operate in a configuration wherein a first of transducers 20 emits and a second of transducers 20 detects the returned echo signal emitted by the first transducer. In such an embodiment, a detecting second transducer can be detecting reflected sound waves concurrently while a first transducer emits sound waves. Such configuration can improve sensitivity of probe 10 as there is reduced risk of a relevant reflection signal being lost.

Regarding signaling configurations of a transducer 20, signaling configurations of transducer 20 can be intermittent or continuous. When a signaling configuration of transducer 20 is intermittent, transducer 20 can be controlled to transition intermittently between emission periods and detection periods as depicted in the timing diagram of FIGS. 31 and 34. When a signaling configuration of transducer 20 is continuous, transducer 20 can continuously emit a waveform without intermittently executing detection periods as depicted by timeline 1012 (FIG. 32) and timeline 1018 (FIG. 35) or continuously detect a reflected waveform without intermittently emitting a waveform as depicted by timeline 1014 (FIG. 32) or timeline 1020 (FIG. 35).

A certain transducer 20 of probe 10 can operate in a plurality of different modes in including a cycling mode and a constant mode.

In a cycling mode, a certain transducer 20 of probe 10 can cycle between an FHR signaling configuration and a UC signaling configuration. A cycling mode can be adaptive or non adaptive. With an adaptive cycling mode active a cycling mode can be exited on (de-activated) the sensing of a sensed condition or on de-energization of probe 10. The sensed condition can be a signal level of a transducer of probe 10. Probe 10 can be configured so that with a non-adaptive cycling mode active probe 10 is restricted from exiting from a cycling mode except for responsively to a de-energization of probe 10. In a constant mode, a certain transducer of probe 10 can be driven in accordance with a certain signaling configuration, e.g., an FHR signaling configuration and a UC signaling configuration. An FHR signaling configuration can be an intermittent emit and detect FHR signaling configuration as indicated by timeline 1010, a continuous emitting FHR signaling configuration as indicated by timeline 1012, a continuous detecting FHR signaling configuration as indicated by timeline 1014. A UC signaling configuration can be an intermittent emit and detect UC signaling configuration as indicated by timeline 1016, a continuous emitting UC signaling configuration as indicated by timeline 1018, a continuous detecting UC signaling configuration as indicated by timeline 1020. A constant mode can be adaptive or non-adaptive. With an adaptive constant mode active, a constant mode can be exited (de-activated) on the sensing of a sensed condition or on de-energization of probe 10. The sensed condition can a signal level of a transducer of probe 10.

Probe 10 can be configured so that with a non-adaptive constant mode active, probe 10 is restricted from exiting a current signaling configuration except for responsively to a de-energization of probe 10.

Figure 36:
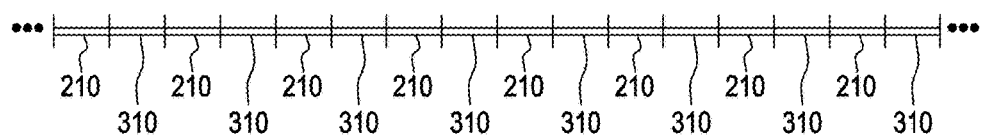
FIG. 36 is timing diagram illustrating operation of a transducer in a cycling mode.

Referring to timing diagram of FIG. 36, timing diagram of FIG. 36 illustrates operation of a probe 10 having a transducer 20 that cycles between operating in an FHR signaling configuration during periods 210 and a uterine contraction (UC) signaling configuration during periods 310. The signaling configurations can be executed on an intermittent or continuous basis as set forth herein. In an FHR signaling configuration, transducer 20 can emit a Doppler ultrasound wave. The respective durations of an FHR signaling periods 210 and a UC signaling periods 310 can be predetermined. When operating in accordance with a cycling mode a switch to a signaling configuration other than the one currently being executed can be predetermined, and in one embodiment can be prevented only by a sensing of a certain sensed condition or a de-energization of probe 10. A UC signaling configuration can be characterized by a pulse wave emission followed by processing of signals representing uterine tissue interfaces. Accordingly, a probe 10 operating in accordance with the timing diagram of FIG. 36 is operative to both detect fetal heart rate and detect uterine contractions. Operation in accordance with the timing diagram of FIG. 36 can be performed with use of a probe having one or more transducer 20.

Figure 37:
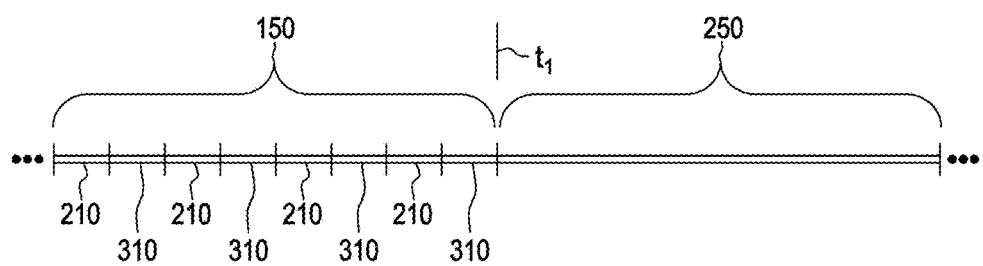
FIG. 37 is timing diagram illustrating operation of a transducer in a cycling mode and switching to a constant mode.

In the embodiment as described in connection with the timing diagram of FIG. 37 transducer 20 during period 150 can be operative in a cycling mode in which it repetitively cycles between FHR and UC signaling and then switches to a constant mode during period 250 in which transducer 20 constantly operates in an FHR signaling configuration for FHR detection without cycling between an FHR signaling configuration and a UC signaling configuration. Alternatively, the constant mode depicted by period 250 can be a UC signaling configuration. A constant mode active during period 250 can be adaptive or non-adaptive. The switching at time $t_1$ can be responsive to a sensed condition. In one embodiment, the sensed condition can be that a signal output by transducer 20 indicates detection of a fetal heart beat. In another embodiment, the cycling mode period 150 can replaced with a constant mode period in which a certain transducer 20 operates in a signaling configuration other than the signaling configuration depicted by period 250. For example period 150 can be a period in which a constant mode UC signaling configuration is active and period 250 can be a period in which a constant mode FHR signaling configuration is active, or vice versa. The transition between signaling configurations can be responsive to a sensed condition, e.g. in the case of UC to FHR signaling configuration transition that the signal output by the certain transducer 20 indicates that fetal heart rate would be detectable with a transition to the FHR the signaling configurations. In the case of an FHR to UC signaling configuration transition the sensed condition can be, e.g., a signal output by the certain transducer 20 indicating a time shift.

In another embodiment, probe 10 in any of the configurations A through E of FIG. 24 is operative so that a signaling configuration of one or more transducer 20 of probe 10 is responsive to a manually input control input by an operator. Probe 10 can be operative so that a constant mode signaling configuration (intermittent or continuous) of any one or more transducer 20 of probe 10 is responsive to a manually input control input using a user interface 70 and/or 170 of system 1000.

Figure 38:
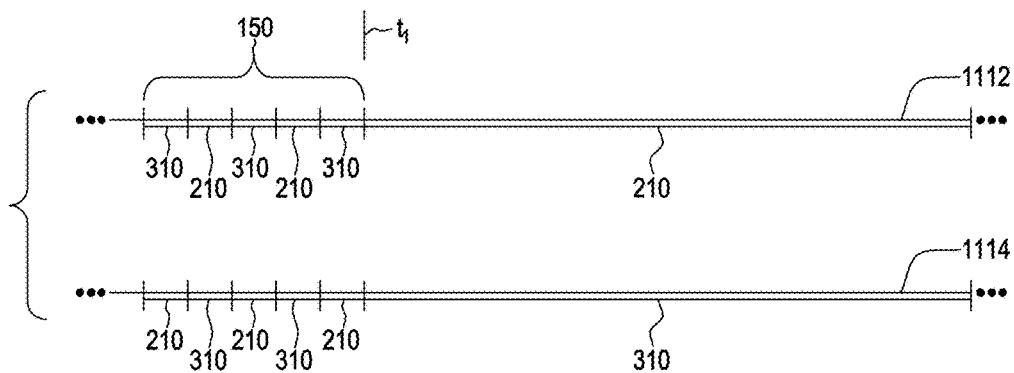
FIG. 38 is a timing diagram illustrating operation of first and second transducers switching operation from a cycling mode to respective constant mode, wherein a constant mode for one of the transducer is an FHR signaling constant mode and a constant mode for a remaining of the transducers is a UC constant mode.

In the embodiment of FIG. 38 there is illustrated operation of a probe 10 having two or more transducers 20 including first and second transducers wherein each of the transducers can operate in a plurality of signaling configuration e.g., both an FHR signaling configuration and a UC signaling configuration. Timeline 1112 illustrates operation of a first transducer and timeline 1114 illustrates operation of a second transducer. The first and second transducers can be, e.g. transducers at locations "b" and "c" of Configuration B, FIG. 24 transducers 20 at locations "d" and "f" of Configuration C, transducers 20 at locations "h" and "g" of Configuration D, transducers 20 at locations "p" and "q" of Configuration E, FIG. 24. During period 150 each of transducers 20 cycle between an FHR signaling configuration and a UC signaling configuration. At time $t_1$ transducer 20 having operations depicted by timeline 1112 ceases cycling between signaling configurations and switches to operating in a constant mode FHR signaling configuration. At time $t_1$ transducer 20, having operation depicted by timeline 1114 ceases cycling and switches to operating in a constant mode UC signaling configuration. The switching at time $t_1$ can be in response to a sensed condition. A sensed condition can be that transducer 20 having operation depicted by timeline 1112 outputs a signal indicative of a fetal heart beat.

Figure 39:
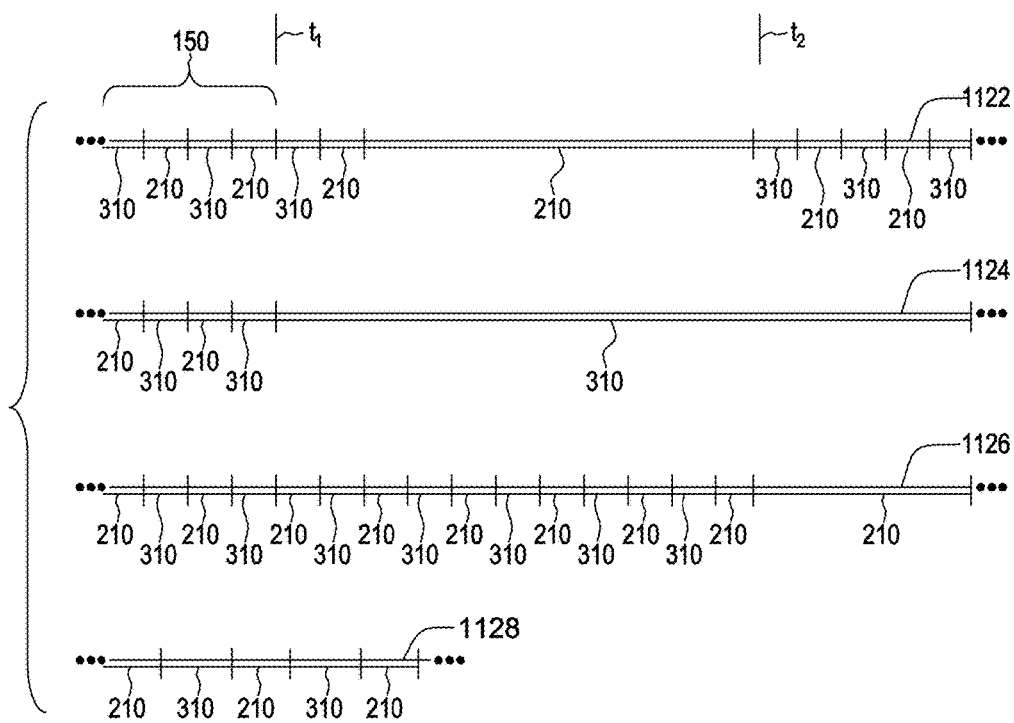
FIG. 39 is a timing diagram illustrating operation of a probe having first and second and third transducers each having switching modes of operation.

With reference to the timing diagram of FIG. 39 there is illustrated operation of a probe 10 having three or more transducers including first, second and third transducers wherein each of the transducers can operate in a plurality of signaling configurations, e.g., both an FHR signaling configuration and a UC signaling configuration. Timeline 1122 illustrates operation of a first transducer 20, timeline 1124 illustrates operation of a second transducer, and timeline 1126 illustrates operation of a third transducer 20. Timelines 1122, 1124, 1128 can represent e.g., operation of transducers 20 at locations "e," "d" and "f" respectively of configuration C, FIG. 24 or, e.g., transducers 20 at locations "k," "m" and "q" of configuration E, FIG. 24, or transducers 20 at location transducers 20 at locations "g," "i" and "j" of configuration D.

During period 150 each of transducers 20 represented by respective timelines 1122, 1124, 1126 operates in accordance with a cycling mode and cycles between an FHR signaling configuration and a UC signaling configuration. At time $t_1$ transducer 20 represented by timeline 1122 ceases cycling between configurations and switches to operating in a constant mode FHR signaling configuration until time $t_2$. At time $t_1$ transducer 20 represented by timeline 1124 ceases cycling between configurations and switches to operating in a constant mode UC signaling configuration represented by period 310 of timeline 1124. Also at time $t_2$ transducer 20 represented by timeline 1122 ceases operating in a constant mode FHR configuration and switches to a cycling mode in which it cycles between an FHR signaling configuration and a UC signaling configuration. Regarding the transducer 20 represented by timeline 1126, the transducer 20 represented by timeline 1126 cycles between operating in an FHR signaling configuration and a UC signaling configuration until time $t_2$. The switching of the transducer represented by timeline 1122 at time $t_1$ can be responsive to a sensed condition, e.g., a signal quality output by a transducer represented by timeline 1122. Signal quality can be determined based on one or more signal parameter, e.g. signal strength and/or a presence of a detectable shift in the signal over time. The switching of the transducer represented by timelines 1122 and 1126 at time t₂ can be responsive to a sensed condition, e.g., a decrease in signal quality of the transducer represented by timeline 1122 and/or an increase in signal quality represented by timeline 1126.

In some embodiments, it can be advantageous to synchronize operation of transducers as indicated by timelines 1122, 1124, 1126, e.g., such operation can improve a capability of a first transducer detecting a sound wave emitted by one or more other transducer. However in some embodiments, e.g., if cross talk avoidance is prioritized, it can be advantageous to de-synchronize operation of two or more transducers. Timeline 1128 illustrates operation of a transducer having operation de-synchronized (by having longer periods 210 and periods 310) relative to neighboring transducers of a probe 10.

A profile of probe 10 can be regarded as the set of operating states of transducers 20 characterizing operation of the probe 10 at a given period in time. A profile of probe 10 illustrated with reference to the timing diagram of FIG. 39 prior to time t₁ is characterized by first second and third transducers operating in a cycling mode of operation, and after time t₁, is characterized by a first transducer operating in a constant mode FHR signaling configuration, and a second transducer operating in a constant mode UC signaling configuration.

Figure 40:
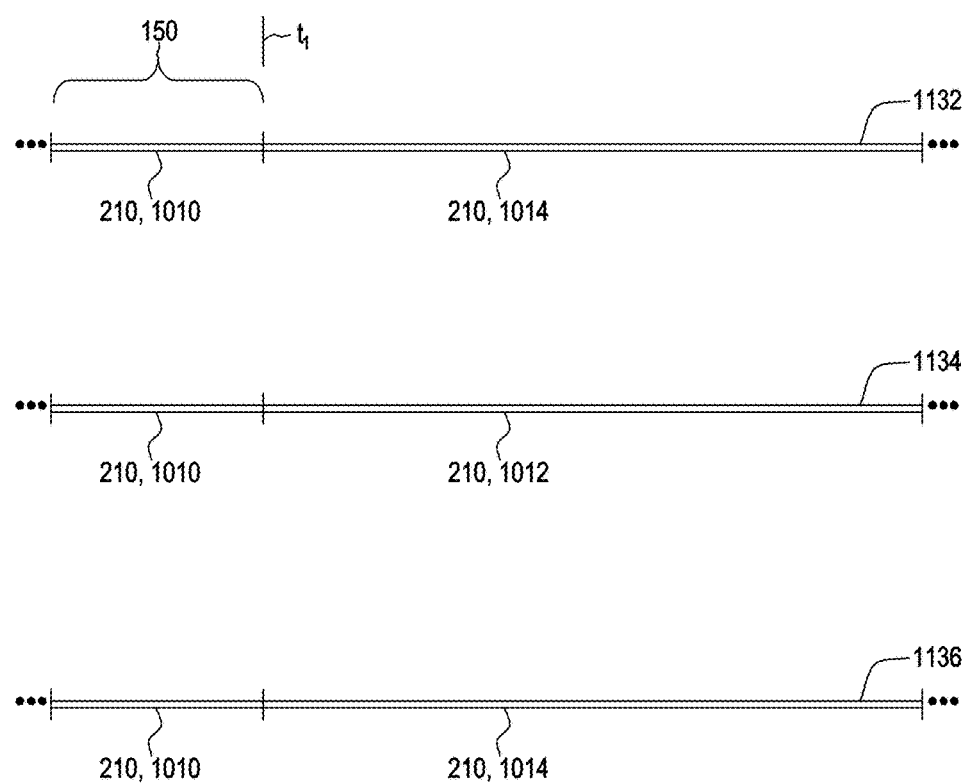
FIG. 40 is a timing diagram illustrating operation of a probe having first and second and third transducers each having transitioning signaling configurations.

With reference to the timing diagram of FIG. 40 there is illustrated operation of a probe 10 having three or more transducers including first, second and third transducers wherein each of the transducers can operate in a either intermittent or continuous signaling configurations. Timeline 1132 illustrates operation of a first transducer 20, timeline 1134 illustrates operation of a second transducer 20, and timeline 1136 can represent operation of a third transducer 20. Timelines 1132, 1134, 1136 can represent e.g., operation of transducers 20 at locations "e," "d" and "f" respectively of configuration C, FIG. 24 or, e.g., transducers 20 at locations "k," "m" and "q" of configuration E, FIG. 24, or transducers 20 at location transducers 20 at locations "g," "i" and "j" of configuration D, FIG. 24.

During period 150 each of transducers 20 represented by respective timelines 1132, 1134, 1136 operates in an intermittently emitting constant mode FHR signaling configuration. At time t₁ transducer 20 represented by timeline 1132 ceases operating in an intermittently emitting constant mode FHR signaling configuration and switches to operating in a constant mode continuously emitting FHR signaling configuration. At time t₁ transducer 20 represented by timeline 1134 ceases operating in an intermittently emitting constant mode FHR signaling configuration and switches to operating in a constant mode continuously detecting FHR signaling configuration. At time t₁ transducer 20 represented by timeline 1136 ceases operating in an intermittently emitting constant mode FHR signaling configuration and switches to operating in a constant mode continuously emitting FHR signaling configuration. The switching of the transducer represented by timelines 1132, 1134, and 1136 at time t₁ can be responsive to a sensed condition, e.g., a signal quality output by one or more transducer represented by timelines 1132, 1134, and 1136. A signal quality can be determined based on one or more signal parameter, e.g. signal strength, a representation of a time or frequency shift by the signal.

In the embodiment described with reference to the timing diagram of FIG. 40, transducers 20 having operation depicted by timelines 1132 and 1136 can, after time t₁, continuously emit a reflected waveform and transducer 20 having operation depicted by timeline 1134, after time t₁ can continuously detect the reflected waveform emitted by the transducers represented by timeline 1132 and 1136. In the embodiment described in connection with FIG. 40 transducers 20 represented by timelines 1132 and 1136 during periods 210, 1014, can emit waveforms continuously per timeline 1012 and transducer 20 depicted by timeline 1134 during period 210, 1012 detects for reflected echo waveforms continuously per timeline 1014. Increasing a number of transducers 20 emitting can increase a signal to noise ratio. As indicated by the timing diagram of FIG. 40, probe 10 can be configured for examining transducer signals output during sampling period 150 and responsively to the examining can activate two or more transducers for emitting sound waveforms and one or more transducer 20 for detecting reflections of the emitted waveforms.

In another embodiment, probe 10 can activate a single transducer for emission and detection, according to timeline 1010, or a single transducer pair according to timelines 1012, 1014 responsively to an examination of transducer signals output during period. Probe 10 can be adapted so that the determination as to whether one or more than one transducer 20 is activated for emission can be responsive to a characteristic of one or more signal examined. For example if during sampling period 150 there is a certain transducer that outputs, by a predetermined margin, the strongest signal, system 1000 can select the certain transducer for emission after time t1. If during sampling period 150 there are first and second transducers 20 that output a signal having an amplitude above a predetermined amplitude, but no single transducer that outputs by the predetermined margin the strongest signal, the first and second transducers can be activated for emission after time t1.

A profile of a probe 10 can be regarded as the set of operating states of transducers 20 characterizing operation of the probe 10 at a given period in time. In the example of the timing diagram of FIG. 40, the profile of probe 10 before time t1, which can be regarded as a first profile, is characterized by a first second and third transducer operating in a constant mode intermittent transmit and receive FHR signaling configuration. After time t1 the profile of probe 10, which can be regarded as a second profile, is characterized by first second and third transducers operating in a constant mode FHR signaling configuration with the transducers 20 represented by timeline 1132 and 1136 operating in a constant mode continuously emit FHR signaling configuration and the transducer 20 represented by timeline 1134 operating in a constant mode continuously receive FHR signaling configuration. With the first profile active the transducer 20 represented by timeline 1134 can detect reflected sound waves emitted by transducers 20 represented by timeline 1132 and 1136 provided there is appropriate coordination between emit and detect periods between the various transducers. With the second profile active the transducer 20 represented by timeline 1134 and operating in a constant mode continuously detect FHR signaling configuration can detect reflected sound waves emitted by the transducers represented by timeline 1132 and timeline 1136 concurrently while the transducers 20 represented by timeline 1132 and 1136, each operating in a constant mode continuously emit FHR signaling configuration in accordance with the second profile, continuously emit sound waves.

With reference to the timing diagrams of FIGS. 37-40 and other embodiments set forth herein, there are illustrated operations of a probe 10 that allow a probe 10 to adapt to a current environment of a probe 10. For example, probe 10 can be adapted so that over time, probe 10 can establish operation of one or more transducer 20 of probe 10 to optimize detection performance of probe 10, e.g., to track a movement of a fetus without necessitating movement of probe 10.

Periods 210 as set forth herein with reference to various timelines can represent (a) a combination of a single period 202 and a successive single period 204 as set forth relative to timeline 1010, (b) a combination of a plurality of intermittently active periods 202 and periods 204 as set forth relative to timeline 1010, (c) a transducer continuously emitting as set forth with reference to timeline 1012, or (d) a transducer continuously detecting as set forth with reference to timeline 1014. Periods 310 as set forth herein with reference to various timelines can represent (a) a combination of a single period 302 and a successive single period 304 as set forth relative to timeline 1016, (b) a combination of a plurality of intermittently active periods 302 and periods 304 as set forth relative to timeline 1016, (c) a transducer continuously emitting as set forth with reference to timeline 1018, or (d) a transducer continuously detecting as set forth with reference to timeline 1020. It will be understood that sampling periods 150 depicted in the various timing diagrams as having a duration of a limited number of signaling configuration periods or emit and detection periods can in practice last for several seconds or minutes or longer or shorter than a time depicted. Further a mode of operation depicted in any timing diagram can have any duration.

Figure 41:
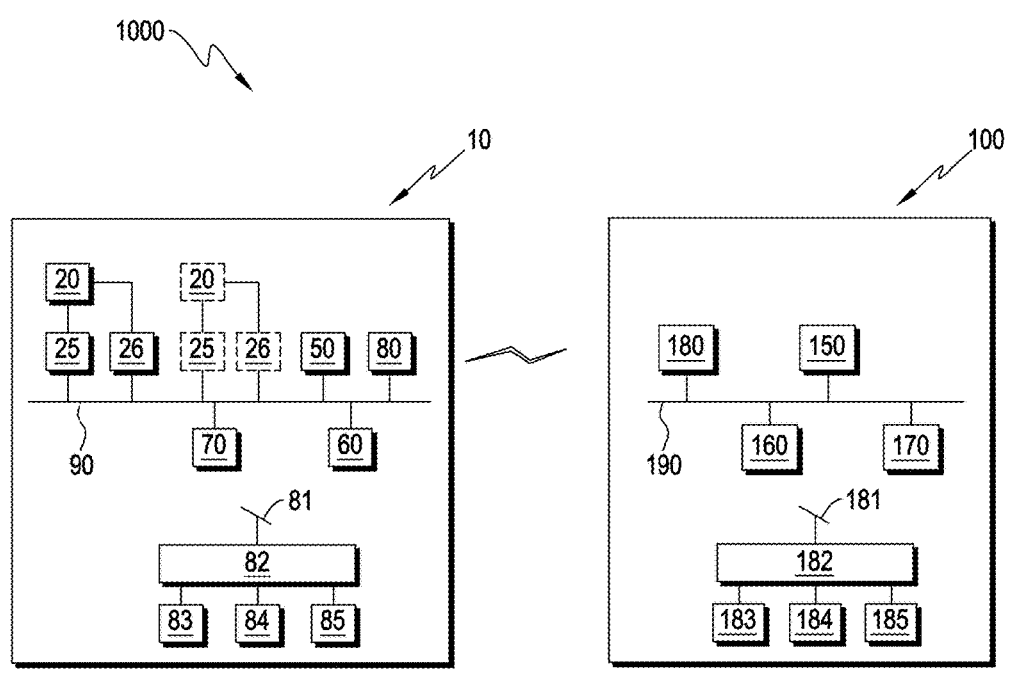
FIG. 41 is a block diagram of a uterine probe system.

It has been mentioned that probe 10 can be interfaced to a commercially available monitoring unit. In one example a monitoring yet, can be a Corometrics monitoring unit. A uterine probe system 1000 having another exemplary monitoring unit 100 is depicted in FIG. 41. Probe 10 can include A/D converters 25 for digitizing signals output by one or more transducer and probe 10 can further include memory 60 and CPU 50 in communication with system bus 90 and can further include communication interface 80 and a user interface 70, e.g., as can be provided by a touch screen. Probe 10 can also include a power grid 81, coupled to a power supply 82 which can be powered alternatively by alternating power sources, e.g., a battery 83, an AC/DC transformer 84, a wireline cable 85, e.g., USB. Probe 10 can further include one or more signal driving circuit 26 for driving (exciting) one or more transducer 20 for emission of sound waves. Monitor unit 100 can also include a CPU 150, a memory 160 a communication interface 180 and well as a user interface 170 (e.g., a touchpad including a display and defined keys). Transducer signals can be digitized and formatted by probe 10 and transmitted to monitoring unit 100 for processing, monitoring unit 100 can also include a power grid 181, coupled to a power supply 182 which can be powered alternatively by alternating power sources, e.g., a battery 183, an AC/DC transformer 184, a wireline cable 185, e.g., USB. While in the embodiment shown in FIG. 41 digitized signals are transmitted by probe 10 to monitor unit 100 system 1000 can be alternatively arranged so that probe 10 transmit analog signals to monitoring unit 100. Shown as separate units, the element of monitoring unit 100 can be co-located with probe, e.g., disposed in a housing of probe 10 and connected to a system bus 90 where appropriate.

The Abstract below is provided to comply with 37 C.F.R. § 1.72(b) to allow the reader to quickly ascertain the nature and gist of the technical disclosure. The Abstract is submitted with the understanding that it will not be used to interpret or limit the scope or meaning of the invention.

A small sample of systems, methods, and apparatus that are described herein is as follows:

A1. An ultrasound probe comprising: a first ultrasound transducer element having a first imaging axis; a second ultrasound transducer element having a second imaging axis; wherein the first imaging axis and the second imaging axis extend in directions that are non-parallel to one another. A2. The ultrasound probe of A1, wherein the first ultrasound transducer element and the second ultrasound transducer element include lenses for diffusing emitted ultrasound waves. A3. The ultrasound probe of A1, wherein the ultrasound probe includes a third ultrasound transducer element having a third imaging axis, the third imaging axis extending in a direction that is non-parallel relative to the first imaging axis and the second imaging axis. A4. The ultrasound probe of A1, wherein the ultrasound probe includes the first and second ultrasound transducer elements, and third, fourth, fifth, sixth and seventh ultrasound transducer elements, the third, fourth, fifth, sixth and seventh ultrasound transducer elements having third, fourth, fifth, sixth and seventh imaging axes, the first to seventh ultrasound transducer elements defining one centrally disposed ultrasound transducer element, with remaining ultrasound transducer elements circumferentially disposed about the centrally disposed ultrasound transducer element, the first, second, third, fourth, fifth, sixth and seventh imaging axis each extending in directions non-parallel to one another. B1. An ultrasound probe comprising: an ultrasound transducer element; a force transducer element; wherein the ultrasound transducer element and the force transducer element are commonly housed. B2. The ultrasound probe of B1, wherein the ultrasound probe comprises a centrally disposed force transducer element and a plurality of circumferentially disposed ultrasound transducer elements. C1. A method comprising: providing a probe having an ultrasound transducer element and a force transducer element, the ultrasound transducer element and the force transducer element being supported in a common housing; and applying the probe to a patient to obtain measurements of both fetal heart rate monitoring and uterine contractions. D1. An ultrasound probe comprising: a first transducer; a second transducer; a carrier supporting the first transducer and the second transducer; a first lens associated to the first transducer, the first lens having a diverging lens setting; a second lens associated to the second transducer, the second lens having a diverging lens setting. D2. The ultrasound probe of D1, wherein the first transducer has a first imaging axis, wherein the second transducer has a second imaging axis, and wherein the first imaging axis and the second imaging axis are non-parallel to one another. D3. The ultrasound probe of D1, wherein the ultrasound probe includes a third transducer, wherein the ultrasound probe includes a third lens associated to the third transducer, the third lens having a diverging setting. D4. The ultrasound probe of D3, wherein the carrier supports the first transducer and the second transducer and the third transducer so that a first line extending perpendicularly through the first transducer and a second line extending perpendicularly through the second transducer and a third line extending perpendicularly through the third transducer are non-parallel. D5. The ultrasound probe of D1, wherein the carrier supports the first transducer and the second transducer so that a line extending perpendicularly through the first transducer and a line extending perpendicularly through the second transducer are non-parallel. D6. The ultrasound probe of D1, wherein the carrier is provided by a material member that includes the first lens and the second lens. D7. The ultrasound probe of D1, wherein the first lens is a spherical lens and the second lens is a cylindrical lens. D8. The uterine probe of D1, wherein the probe includes a center disposed transducer and three or more peripherally disposed transducers, wherein the peripherally disposed transducers have associated lenses and wherein the center disposed transducer is devoid of an associated lens, the probe being configured so that a distal end of the probe defines a generally concave shape with a center region of the distal end extending to a lesser extent than a plurality of points outward relative to the center region. D9. The probe of D1, wherein the probe includes a center disposed transducer and three or more peripherally disposed transducers, wherein the peripherally disposed transducers have associated lenses and wherein the center disposed transducer is devoid of an associated lens. E1. A method comprising: emitting a sound wave so that the sound wave reflects from a tissue interface; receiving a reflected sound wave; and determining a uterine contraction parameter utilizing the reflected sound wave. E2. The method of E1, wherein the determining includes determining a distance between echoes. F1. A system comprising: a transducer disposed on uterine probe for emitting a sound wave so that the sound wave is reflected from a tissue interface; wherein the probe is operative for detection of the reflected sound wave reflected from the tissue interface; wherein the system is operative to determine a uterine detection parameter utilizing the reflected sound wave. F2. The system of F1, wherein the system determines a strength of a uterine contraction utilizing the reflected sound wave. F3. The system of F1, wherein the system displays on a display a line graph wherein peaks of the line graph indicate contractions, and wherein a size of peaks of the line graph indicate contraction strength as determined utilizing the reflected sound wave. G1. A uterine probe comprising: one or more transducer emitting a first sound wave and a second sound wave; wherein the uterine probe is configured so that a signal representing the first sound waves reflected from a target is processed for fetal heart rate (FHR) determination and further so that a signal representing the second sound wave reflected from a target is processed for uterine contraction (UC) determination. G2. The uterine probe of G1, wherein the uterine probe comprises a certain transducer that emits the first sound wave and the second sound wave. G3. The uterine probe of G1, wherein the uterine probe comprises a first transducer emitting the first sound wave and a second transducer emitting the second sound wave. H1. A uterine probe comprising: a transducer; wherein the transducer is operative for transitioning between a first signaling configuration for detection of a first uterine parameter and a second signaling configuration for detection of a second uterine parameter. H2. The uterine probe of H1, wherein the first uterine parameter is a fetal heart rate (FHR) parameter, and wherein the second parameter is uterine contraction (UC) parameter. H3. The uterine probe of H1, wherein the uterine probe is operative in a cycling mode of operation in which the uterine probe repetitively activates each of the first signaling configuration and the second signaling configuration. H4. The uterine probe of H1, wherein the uterine probe is operative so that the transitioning is performed responsively to a manually input control input by an operator. H5. The uterine probe of H1, wherein the uterine probe is operative so that the transitioning is performed responsively to a sensed condition. I1. A uterine probe comprising: a first transducer; a second transducer; wherein the uterine probe operates in accordance with a first profile in which the first transducer and the second transducer operate in respective cycling modes of operation in which the first transducer and the second transducer cycle between operating in a fetal heart rate (FHR) signaling configuration and a uterine contraction (UC) signaling configuration. I2. The uterine probe of I1, wherein responsively to a sensed condition the first transducer transitions from the cycling mode of operation to a constant mode of operation in which the first transducer operates in an FHR signaling configuration. I3. The uterine probe of I1, wherein the uterine probe further operates in accordance with a second profile in which the first transducer operates in a constant mode FHR signaling configuration and the second transducer operates in a constant mode UC signaling configuration, and wherein the uterine probe transitions from the first profile to the second profile responsively to a sensed condition. J1. A uterine probe comprising: a first transducer; a second transducer; a third transducer; wherein the uterine probe is operative in accordance with a profile in which the first transducer detects for reflected sound waves emitted by each of the first transducer and the second transducer. J2. The uterine probe of J1, wherein the first transducer and the second transducer, in accordance with the profile emit sound waves concurrently while the third transducer detects for the reflected sound waves emitted by each of the first transducer and the second transducer. J3. The uterine probe of J2, wherein the first transducer and the second transducer, in accordance with the profile, operate in a constant mode continuously emit FHR signaling configuration, and wherein the third transducer, in accordance with the profile, operates in constant mode continuously detect FHR signaling configuration. J4. The uterine probe of J1, wherein the probe includes a center disposed transducer and three or more peripherally disposed transducers, wherein the peripherally disposed probes have associated lenses and wherein the center disposed transducer is devoid of a lens, the probe being configured so that a distal end of the probe defines a generally concave shape with a center region of the distal end extending to a lesser extent than a plurality of points outward relative to the center region. K1. A uterine probe: one or more transducer; wherein the uterine probe is configured to emit a beam profile; wherein the uterine probe is configured so that the beam profile is shaped to coincide with a detection area delimited by physiological attributes of a patient's body. K2. The uterine probe of K1, wherein the one or more transducer includes a first transducer and a second transducer, wherein the first transducer includes a first associated lens and wherein the second transducer includes a second associated lens, wherein the first associated lens and the second associated lens are of different lens types. K3. The uterine probe of K1, wherein the one or more transducer includes a first transducer and a second transducer, wherein the first transducer includes a first associated lens and wherein the second transducer includes a second associated lens, wherein the first associated lens and the second associated lens are of different lens sizes. K4. The uterine probe of K1, wherein the uterine probe includes a plurality of transducers arranged in an asymmetrical formation. K5. The uterine probe of K1, wherein the uterine probe includes first and second sound wave emitting transducers of different sizes.

While the present invention has been described with reference to a number of specific embodiments, it will be understood that the true spirit and scope of the invention should be determined only with respect to claims that can be supported by the present specification. Further, while in numerous cases herein wherein systems and apparatuses and methods are described as having a certain number of elements it will be understood that such systems, apparatuses and methods can be practiced with fewer than or greater than the mentioned certain number of elements. Also, while a number of particular embodiments have been described, it will be understood that features and aspects that have been described with reference to each particular embodiment can be used with each remaining particularly described embodiment.

The invention claimed is:

1. An ultrasound probe comprising:
    a first transducer;
    a second transducer;
    a carrier supporting the first transducer and the second transducer;
    a first lens associated to the first transducer, the first lens having a diverging lens setting; and
    a second lens associated to the second transducer, the second lens having a diverging lens setting, wherein the probe includes a center disposed transducer and three or more peripherally disposed transducers including the first transducer and the second transducer, wherein the peripherally disposed transducers have associated lenses and wherein the center disposed transducer is devoid of an associated lens, wherein the carrier supports the first transducer and the second transducer so that a line extending perpendicularly through an active front face surface of the first transducer and a line extending perpendicularly through an active front face surface of the second transducer are non-parallel.

2. The ultrasound probe of claim 1, wherein the first transducer has a first imaging axis, wherein the second transducer has a second imaging axis, and wherein the first imaging axis and the second imaging axis are non-parallel to one another.

3. The ultrasound probe of claim 1, wherein the ultrasound probe includes a third transducer, wherein the ultrasound probe includes a third lens associated to the third transducer, the third lens having a diverging lens setting.

4. The ultrasound probe of claim 1, wherein the carrier is provided by a material member that includes the first lens and the second lens.

5. The ultrasound probe of claim 1, the probe being configured so that a distal end of the probe defines a generally concave shape with a center region of the distal end extending to a lesser extent than a plurality of points outward relative to the center region.

6. An ultrasound probe comprising:
    a first transducer;
    a second transducer;
    a carrier supporting the first transducer and the second transducer;
    wherein the first transducer is associated to a first lens, the first lens having a diverging lens setting, wherein other than the first transducer the ultrasound probe is absent of a transducer that is associated to the first lens; and
    wherein the second transducer is associated to a second lens, the second lens having a diverging lens setting, wherein other than the second transducer the ultrasound probe is absent of a transducer that is associated to the second lens, wherein the carrier supports the first transducer and the second transducer so that a line extending perpendicularly through an active front face surface of the first transducer and a line extending perpendicularly through an active front face surface of the second transducer are non-parallel.

7. The ultrasound probe of claim 6, wherein the first transducer has a first imaging axis, wherein the second transducer has a second imaging axis, and wherein the first imaging axis and the second imaging axis are non-parallel to one another.

8. The ultrasound probe of claim 6, wherein the ultrasound probe includes a third transducer, wherein the ultrasound probe includes a third lens associated to the third transducer, the third lens having a diverging setting.

9. The ultrasound probe of claim 8, wherein the carrier supports the first transducer and the second transducer and the third transducer so that a first line extending perpendicularly through an active front face surface of the first transducer and a second line extending perpendicularly through an active front face surface of the second transducer and a third line extending perpendicularly through an active front face surface of the third transducer are non-parallel.

10. The ultrasound probe of claim 6, wherein the carrier is provided by a material member that includes the first lens and the second lens.

11. The ultrasound probe of claim 6, wherein the first lens is a spherical lens and the second lens is a cylindrical lens.

12. The probe of claim 6, wherein the probe includes a center disposed transducer and three or more peripherally disposed transducers, wherein the peripherally disposed transducers have associated lenses and wherein the center disposed transducer is devoid of an associated lens.

13. The probe of claim 6, wherein ultrasound signals are emitted from the first transducer and the second transducer simultaneously.

14. The probe of claim 6, wherein a signal output by one or more of the first transducer or the second transducer is processed for fetal heart rate monitoring.

15. The probe of claim 6, wherein a signal output by one or more of the first transducer or the second transducer is processed for uterine contraction detection.

16. The probe of claim 6, wherein the first transducer is driven in a signaling configuration for fetal heart rate detection.

17. The probe of claim 6, wherein the first transducer is driven in a signaling configuration for uterine contraction detection.

18. The probe of claim 6, wherein the probe is operative so that the first transducer is driven in a first signaling configuration for uterine contraction detection and in a second signaling configuration for fetal heart rate detection.

19. The ultrasound probe of claim 6, wherein the first lens is a spherical lens and the second lens is a cylindrical lens, wherein the ultrasound probe includes a plurality of transducers including the first transducer and the second transducer, wherein the ultrasound probe is configured including with use of the spherical lens in combination with the cylindrical lens to project an asymmetrical ultrasound beam profile, wherein the ultrasound probe is configured so that the asymmetrical ultrasound beam profile has a shape corresponding to a shape of an asymmetrical region of a patient's body.

20. The ultrasound probe of claim 6, wherein the carrier supports the first transducer and the second transducer so that a first line extending perpendicularly through an active front face surface of the first transducer and a second line extending perpendicularly through an active front face surface of the second transducer are non-parallel, and wherein the carrier supports the first transducer and the second transducer so that the first line and the second line diverge from one another throughout their lengths.

21. An ultrasound probe comprising:
    a first transducer;
    a second transducer;
    a carrier supporting the first transducer and the second transducer;
    a first lens associated to the first transducer, the first lens having a diverging lens setting; and a second lens associated to the second transducer, the second lens having a diverging lens setting, wherein ultrasound signals are emitted from the first transducer and the second transducer simultaneously, wherein a line extending perpendicularly through an active front face surface of the first transducer and a line extending perpendicularly through an active front face surface of the second transducer are non-parallel.

22. An ultrasound probe comprising:
a first transducer;
a second transducer;
a carrier supporting the first transducer and the second transducer;
wherein the first transducer is associated to a first lens, the first lens having a diverging lens setting, wherein other than the first transducer the ultrasound probe is absent of a transducer that is associated to the first lens;
wherein the second transducer is associated to a second lens, the second lens having a diverging lens setting, wherein other than the second transducer the ultrasound probe is absent of a transducer that is associated to the second lens; and
wherein the first lens is a spherical lens and the second lens is a cylindrical lens, wherein the ultrasound probe includes a plurality of transducers including the first transducer and the second transducer, wherein the ultrasound probe is configured including with use of the spherical lens in combination with the cylindrical lens to project an asymmetrical ultrasound beam profile, wherein the ultrasound probe is configured so that the asymmetrical ultrasound beam profile has a shape corresponding to a shape of an asymmetrical region of a patient's body.

23. The ultrasound probe of claim 22, wherein the carrier supports the first transducer and the second transducer so that a line extending perpendicularly through an active front face surface of the first transducer and a line extending perpendicularly through an active front face surface of the second transducer are non-parallel.

24. The ultrasound probe of claim 22, wherein the carrier supports the first transducer and the second transducer so that a line extending perpendicularly through an active front face surface of the first transducer and a line extending perpendicularly through an active front face surface of the second transducer are non-parallel.

25. The ultrasound probe of claim 22, wherein the asymmetrical region of a patient's body is provided by a uterine area combined with a vaginal area of a patient's body.

26. The ultrasound probe of claim 22, wherein the asymmetrical region of a patient's body is provided by a uterine area combined with a vaginal area of a patient's body, wherein from a bottom probe view the probe includes a first row of transducers, a second row of transducers, and a third row of transducers, wherein a plurality of transducers of the first row include associated spherical lenses, wherein a transducer of the second row includes an associated cylindrical lens, and wherein a transducer of the third row includes an associated spherical lens.

27. The probe of claim 22, wherein the first transducer is driven in a signaling configuration for fetal heart rate detection.

28. An ultrasound probe comprising:
a first transducer;
a second transducer;
a carrier supporting the first transducer and the second transducer;
wherein the first transducer is associated to a first lens, the first lens having a diverging lens setting, wherein other than the first transducer the ultrasound probe is absent of a transducer that is associated to the first lens; and
wherein the ultrasound probe is operative so that the first transducer is driven in a first signaling configuration for uterine contraction detection and in a second signaling configuration for fetal heart rate detection, and wherein the ultrasound probe in response to a sensed condition automatically transitions between driving the first transducer in the first signaling configuration for uterine contraction detection, and driving the first transducer in the second signaling configuration for fetal heart rate detection.

29. The ultrasound probe of claim 28, wherein a line extending perpendicularly through an active front face surface of the first transducer and a line extending perpendicularly through an active front face surface of the second transducer are non-parallel.

30. The ultrasound probe of claim 28, wherein the ultrasound probe is operative so that the first transducer is driven in a first signaling configuration for uterine contraction detection and in a second signaling configuration for fetal heart rate detection, wherein the first signaling configuration is characterized by a pulse wave being emitted by the first transducer followed by processing of signals representing uterine tissue interfaces and the ultrasound probe detecting contractions based on examining of time shifts of signal peaks representing tissue interfaces and wherein the second signaling configuration is characterized by the first transducer emitting a burst wave and the ultrasound probe detecting heart rate based on a Doppler frequency shift of a reflected wave, and wherein the ultrasound probe in response to a sensed condition automatically transitions between driving the first transducer in the first signaling configuration for uterine contraction detection, and driving the first transducer in the second signaling configuration for fetal heart rate detection, and wherein sensing the sensed condition includes examining a signal output by an ultrasound transducer of the ultrasound probe.

31. The ultrasound probe of claim 22, wherein the ultrasound probe is operative so that the first transducer is driven in a first signaling configuration for uterine contraction detection and in a second signaling configuration for fetal heart rate detection, and wherein the ultrasound probe in response to a sensed condition automatically transitions between driving the first transducer in the first signaling configuration for uterine contraction detection, and driving the first transducer in the second signaling configuration for fetal heart rate detection.

32. The ultrasound probe of claim 22, wherein the asymmetrical region of a patient's body is provided by a uterine area combined with a vaginal area of a patient's body, wherein from a bottom probe view the ultrasound probe includes a first row of transducers, a second row of transducers, and a third row of transducers, wherein a plurality of transducers of the first row include associated spherical lenses, wherein a transducer of the second row includes an associated cylindrical lens, and wherein a transducer of the third row includes an associated spherical lens, wherein the carrier supports the first transducer and the second transducer so that a first line extending perpendicularly through an active front face surface of the first transducer and a second line extending perpendicularly through an active front face surface of the second transducer are non-parallel, and wherein the carrier supports the first transducer and the second transducer so that the first line and the second line diverge from one another throughout their lengths, and wherein the ultrasound probe is operative so that the first transducer is driven in a first signaling configuration for uterine contraction detection and in a second signaling configuration for fetal heart rate detection, wherein the first signaling configuration is characterized by a pulse wave being emitted by the first transducer followed by processing by the ultrasound probe of signals representing uterine tissue interfaces and detecting contractions based on examining of time shifts of signal peaks representing tissue interfaces and wherein the second signaling configuration is characterized by the first transducer emitting a burst wave and the ultrasound probe detecting heart rate based on a Doppler frequency shift of a reflected wave, and wherein the ultrasound probe in response to a sensed condition automatically transitions between driving the first transducer in the first signaling configuration for uterine contraction detection, and driving the first transducer in the second signaling configuration for fetal heart rate detection, and wherein sensing the sensed condition includes examining a signal output by an ultrasound transducer of the ultrasound probe.

33. The ultrasound probe of claim 28, wherein sensing the sensed condition includes examining a signal output by an ultrasound transducer of the ultrasound probe.

34. The ultrasound probe of claim 28, wherein the ultrasound probe includes a third transducer, wherein the ultrasound probe includes a third lens associated to the third transducer, the third lens having a diverging setting.

35. The probe of claim 22, wherein the probe is operative so that the first transducer is driven in a first signaling configuration for uterine contraction detection and in a second signaling configuration for fetal heart rate detection.

* * * * *

UNITED STATES PATENT AND TRADEMARK OFFICE
CERTIFICATE OF CORRECTION

PATENT NO. : 10,092,271 B2  
APPLICATION NO. : 14/110866  
DATED : October 9, 2018  
INVENTOR(S) : Lewis, Jr. et al.

Page 1 of 1

It is certified that error appears in the above-identified patent and that said Letters Patent is hereby corrected as shown below:

On the Title Page

In the Related U.S. Application Data (60): Delete "Provisional application No. 61/472,087, filed on Apr. 13, 2011." and insert -- Provisional application No. 61/475,087, filed on Apr. 13, 2011 --

Signed and Sealed this  
Twelfth Day of March, 2019

Andrei Iancu  
*Director of the United States Patent and Trademark Office*